(12) United States Patent
Matsuura et al.

(10) Patent No.: US 10,966,677 B2
(45) Date of Patent: Apr. 6, 2021

(54) RADIOGRAPHY APPARATUS

(71) Applicant: FUJIFILM Corporation, Tokyo (JP)

(72) Inventors: Masayoshi Matsuura, Kanagawa (JP); Kazuhiro Makino, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/579,855

(22) Filed: Sep. 24, 2019

(65) Prior Publication Data
US 2020/0100747 A1 Apr. 2, 2020

(30) Foreign Application Priority Data

Sep. 27, 2018 (JP) ............... JP2018-182726

(51) Int. Cl.
*A61B 6/00* (2006.01)
*A61B 6/02* (2006.01)
*A61B 6/04* (2006.01)
*A61B 6/10* (2006.01)

(52) U.S. Cl.
CPC ............. *A61B 6/502* (2013.01); *A61B 6/025* (2013.01); *A61B 6/0414* (2013.01); *A61B 6/107* (2013.01); *A61B 6/4417* (2013.01); *A61B 6/4441* (2013.01); *A61B 6/482* (2013.01); *A61B 6/545* (2013.01); *A61B 6/584* (2013.01)

(58) Field of Classification Search
CPC ....... A61B 6/502; A61B 6/025; A61B 6/0414; A61B 6/107; A61B 6/4441; A61B 6/584; A61B 6/545; A61B 6/482; A61B 6/4417; A61B 6/027; A61B 6/4007; A61B 6/4411; A61B 6/5205; A61B 6/4452
See application file for complete search history.

(56) References Cited

U.S. PATENT DOCUMENTS

| | | | | |
|---|---|---|---|---|
| 2009/0022264 | A1* | 1/2009 | Zhou | A61B 6/025 378/5 |
| 2009/0323893 | A1* | 12/2009 | Hanke | A61B 6/025 378/37 |
| 2011/0122992 | A1* | 5/2011 | Hanke | H01J 35/10 378/37 |
| 2012/0008739 | A1* | 1/2012 | Hoernig | A61B 6/502 378/37 |

FOREIGN PATENT DOCUMENTS

| | | |
|---|---|---|
| JP | 2016-135319 | 7/2016 |
| WO | 2010-028208 | 3/2010 |

* cited by examiner

*Primary Examiner* — Courtney D Thomas
(74) *Attorney, Agent, or Firm* — JCIPRNET

(57) ABSTRACT

A radiography apparatus includes: a radiation detector having an imaging surface that detects radiation transmitted through an object and captures a projection image of the object; and a radiation source that has a plurality of radiation tubes which emit the radiation to the imaging surface at different irradiation angles and includes a plurality of units in which the plurality of radiation tubes are divided and accommodated.

21 Claims, 28 Drawing Sheets

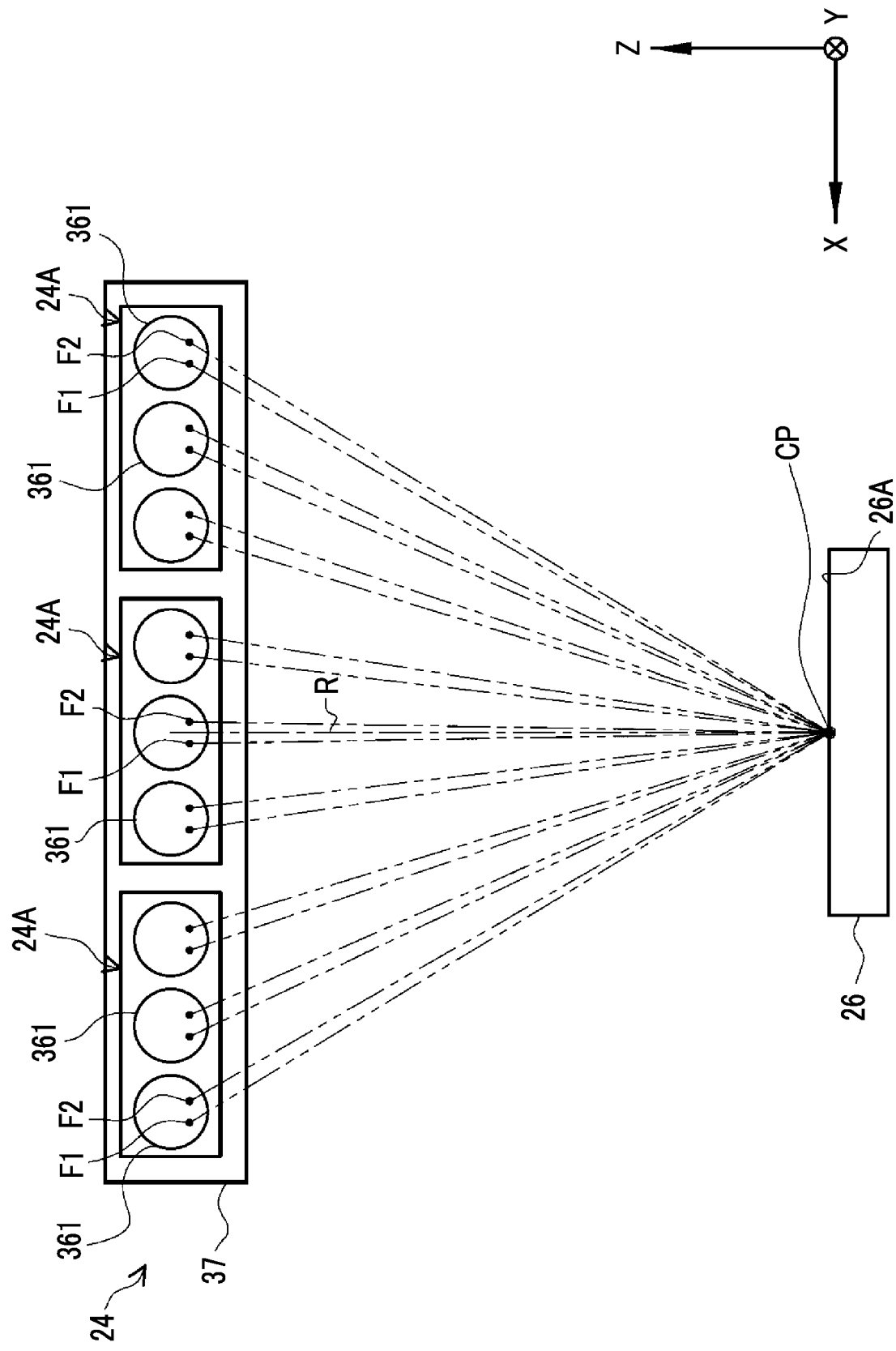

RADIOGRAPHY APPARATUS

CROSS-REFERENCE TO RELATED APPLICATIONS

The present application claims priority under 35 U.S.C. § 119 to Japanese Patent Application No. 2018-182726, filed on Sep. 27, 2018. The above application is hereby expressly incorporated by reference, in its entirety, into the present application.

BACKGROUND

1. Technical Field

The technology according to the present disclosure relates to a radiography apparatus.

2. Description of the Related Art

In the medical field, an X-ray imaging apparatus using radiation, for example, X-rays has been known. Some X-ray imaging apparatuses have a tomosynthesis imaging function. The X-ray imaging apparatus comprises an X-ray detector, an X-ray source, and a movement mechanism for moving the X-ray source (for example, see JP2016-135319A). The X-ray detector has an image surface which is a two-dimensional plane as an imaging surface that detects X-rays transmitted through an object and captures a projection image of the object. The X-ray source includes one X-ray tube that irradiates the object with X-rays. The movement mechanism moves the X-ray source to change the irradiation angle of X-rays emitted from one X-ray tube with respect to the imaging surface.

In one tomosynthesis imaging operation, one X-ray tube emits X-rays at a plurality of different irradiation angles while being moved to acquire a plurality of projection images with different irradiation angles. A tomographic image of a tomographic plane at any position of the object is reconstructed on the basis of the plurality of acquired projection images. The tomosynthesis imaging is used for, for example, mammography using the breast as the object.

SUMMARY

The X-ray imaging apparatus according to the related art, such as the X-ray imaging apparatus disclosed in JP2016-135319A, performs tomosynthesis imaging while moving one X-ray tube. Therefore, the imaging time required for tomosynthesis imaging is longer than that in simple X-ray imaging which captures images in a state in which one X-ray tube is fixed. Moreover, in the tomosynthesis imaging, in addition to the movement of one X-ray tube, the X-ray tube is stopped whenever X-rays are emitted, which also causes an increase in the imaging time.

Since the long imaging time is painful for the object, there is a demand to reduce the imaging time in the tomosynthesis imaging as much as possible.

Therefore, the inventors have studied a technique which provides a plurality of X-ray tubes with different irradiation angles in an X-ray imaging apparatus in order to reduce the imaging time. This technique makes it possible to reduce the imaging time since the X-ray tubes are not moved.

In addition, the inventors consider that the X-ray imaging apparatus including a plurality of X-ray tubes with different irradiation angles is useful in X-ray imaging other than tomosynthesis imaging, for example, fluoroscopic radiography performed during surgery. Therefore, the inventors have examined the development of an X-ray imaging apparatus including a plurality of X-ray tubes.

However, in a case in which a plurality of X-ray tubes are provided, there is a concern that maintenance will deteriorate by an amount corresponding to an increase in the number of X-ray tubes, as compared to a case in which one X-ray tube is provided.

For example, in the configuration in which all of the X-ray tubes are integrated into one unit, even in a case in which only some of the X-ray tubes are broken, it is necessary to replace all of the X-ray tubes including the X-ray tubes which have not been broken. In a case in which all of the X-ray tubes are replaced, it is necessary to adjust the focal position and output of all of the replaced X-ray tubes. As a result, a maintenance operation becomes complicated. In addition, in a case in which all of the X-ray tubes including the X-ray tubes which have not been broken need to be replaced, there is a concern that the cost of components will increase and the maintenance cost will increase. Therefore, it is necessary to take measures to solve the problem of the deterioration of maintenance in a case in which a plurality of X-ray tubes are provided.

An object of the technology according to the present disclosure is to provide a radiography apparatus that can suppress the deterioration of maintenance in a case in which a plurality of X-ray tubes are provided.

In order to achieve the object, a radiography apparatus according to the present disclosure comprises: a radiation detector having an imaging surface that detects radiation transmitted through an object and captures a projection image of the object; and a radiation source that has a plurality of radiation tubes which emit the radiation to the imaging surface at different irradiation angles, selectively irradiates the object with the radiation from the plurality of radiation tubes, and includes a plurality of units in which the plurality of radiation tubes are divided and accommodated.

Preferably, the plurality of radiation tubes are arranged in a row in the radiation source.

Preferably, the radiography apparatus further comprises: an accommodation portion that accommodates the radiation source and the radiation detector at a posture where the radiation source and the radiation detector face each other; and a connection portion that connects the accommodation portion to a base such that the accommodation portion is displaceable with respect to the base.

Preferably, the radiography apparatus further comprises: a voltage generation device that is provided outside the accommodation portion; at least one voltage cable that supplies a voltage generated by the voltage generation device to the radiation source and extends from the voltage generation device into the accommodation portion through the connection portion; and a distribution unit that is provided in the accommodation portion and distributes the voltage supplied through the voltage cable to each of the plurality of units of the radiation source.

Preferably, the distribution unit is a power distribution unit that includes a plurality of connectors for connection to each of the plurality of units and distributes the voltage supplied through the voltage cable to the plurality of units.

Preferably, the voltage cable is connected to one first unit among the plurality of units, and the distribution unit distributes the voltage from the first unit connected to the voltage cable to other second units using a daisy chain method and includes a distribution connector provided in the first unit and a distribution cable connected to the distribution connector.

Preferably, the accommodation portion includes a radiation source accommodation portion accommodating the radiation source and including a plurality of sub-radiation source accommodation portions each of which accommodates at least one of the units.

The object is, for example, the breast.

Preferably, the accommodation portion includes a radiation source accommodation portion that accommodates the radiation source, and both ends of the radiation source accommodation portion in an arrangement direction of the plurality of radiation tubes are inclined toward the radiation detector.

Preferably, the accommodation portion includes a radiation source accommodation portion that accommodates the radiation source, a detector accommodation portion that accommodates the radiation detector, and a support portion that integrally supports the radiation source accommodation portion and the detector accommodation portion, and at least a part of the radiation source accommodation portion is displaceable with respect to the support portion and the detector accommodation portion.

Preferably, at least one of both ends of the radiation source accommodation portion in the arrangement direction of the plurality of radiation tubes is displaceable in a direction away from the radiation detector.

Preferably, the radiation source accommodation portion is slidable along the arrangement direction of the plurality of radiation tubes in a plane parallel to the imaging surface.

Preferably, the radiation source accommodation portion is slidable along a direction perpendicular to the arrangement direction of the plurality of radiation tubes in a plane parallel to the imaging surface.

Preferably, in a case in which an end of the radiation source accommodation portion which is close to the support portion is a rear end, a leading end of the radiation source accommodation portion which is a free end opposite to the rear end is rotatable around the rear end in a direction away from the radiation detector.

Preferably, the radiation tube includes a cathode that emits electrons and an anode that emits radiation from a focus where the electrons emitted from the cathode collide.

Preferably, the anode is a fixed anode.

Preferably, the cathode is a field emission type that emits an electron beam using a field emission phenomenon which occurs in a case in which an electric field is applied to a surface of a conductor.

Preferably, at least one of the plurality of radiation tubes has a plurality of the focuses.

Preferably, the radiography apparatus has a tomosynthesis imaging function which selectively performs the emission of the radiation from the plurality of radiation tubes to acquire a plurality of the projection images based on the emission of the radiation in order to obtain a tomographic image of the object on the basis of the plurality of projection images.

Preferably, during one tomosynthesis imaging operation, the position and posture of the radiation detector are fixed.

According to the technique of the present disclosure, it is possible to suppress the deterioration of maintenance in a case in which a plurality of X-ray tubes are provided.

BRIEF DESCRIPTION OF THE DRAWINGS

Exemplary embodiments according to the technique of the present disclosure will be described in detail based on the following figures, wherein:

FIG. 28 is a diagram illustrating an X-ray tube with a plurality of focuses.

DETAILED DESCRIPTION

First Embodiment

Figure 1:
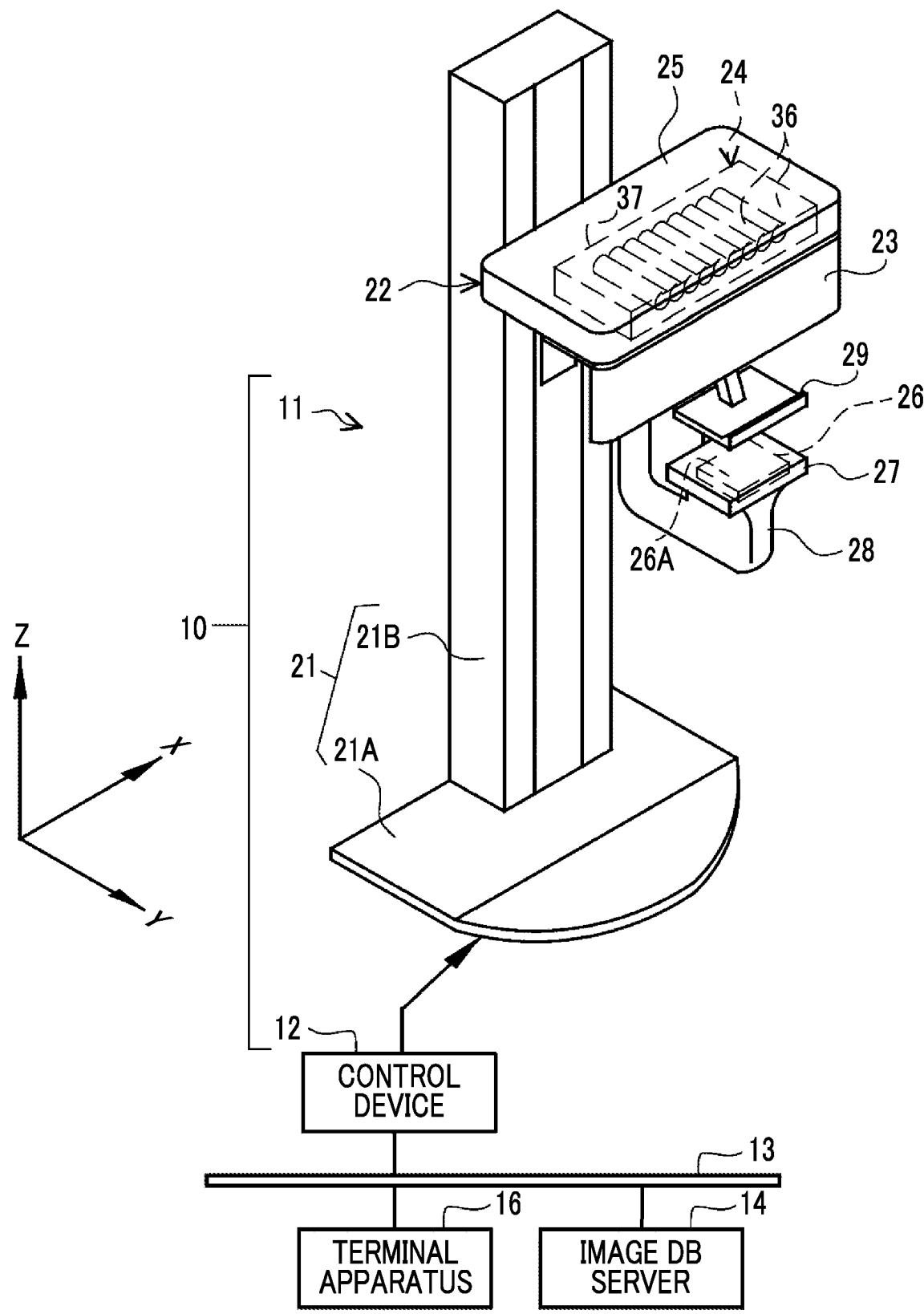
FIG. 1 is a diagram illustrating the outward appearance of a mammography apparatus.
Figure 2:
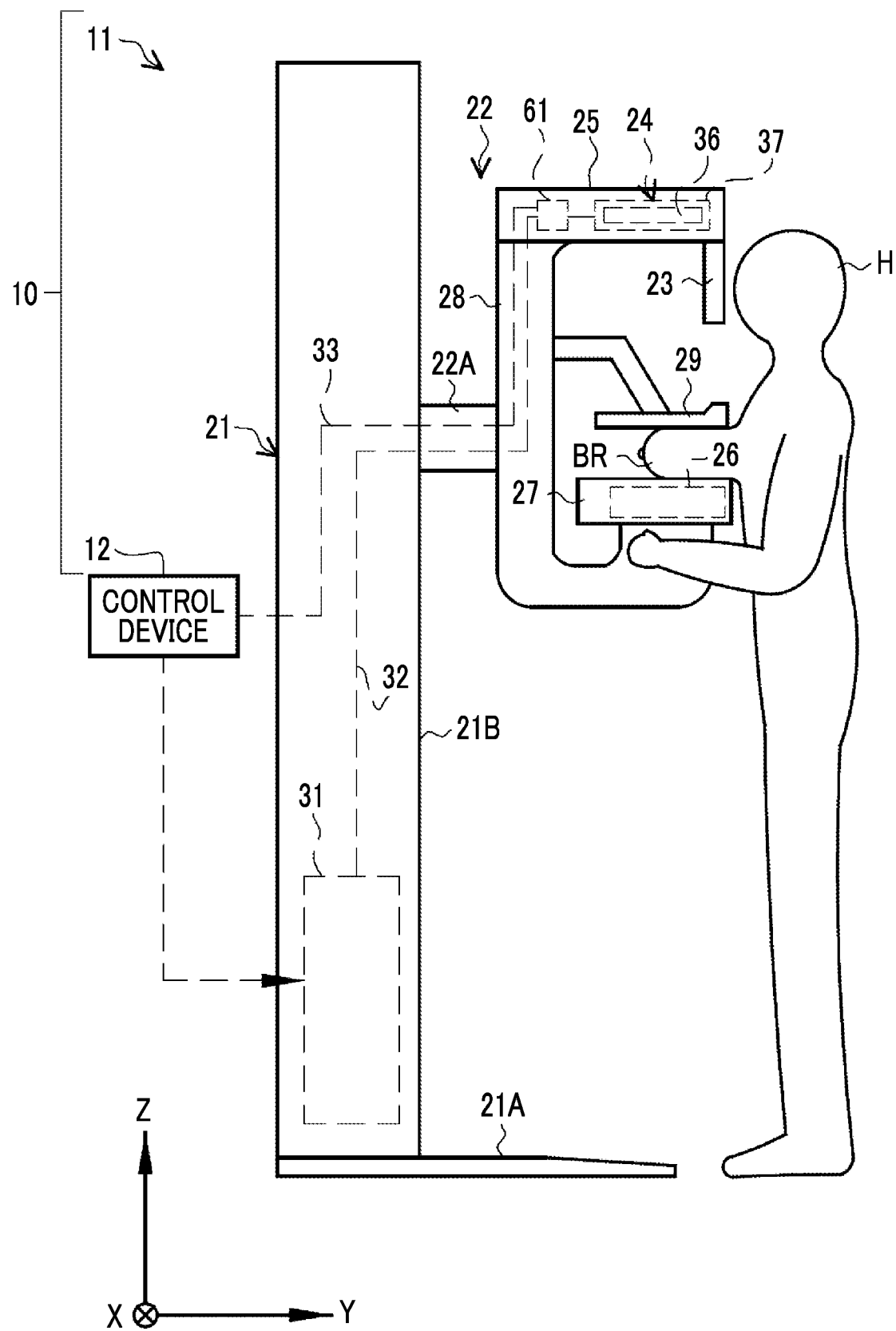
FIG. 2 is a side view illustrating the mammography apparatus.

A mammography apparatus 10 illustrated in FIGS. 1 and 2 irradiates a breast BR of a subject H, which is an object, with X-rays and captures an X-ray image of the breast BR. The mammography apparatus 10 has a tomosynthesis imaging function and is an example of a radiography apparatus. The mammography apparatus 10 includes an apparatus main body 11 and a control device 12.

The control device 12 is connected to an image database (DB) server 14 and a terminal apparatus 16 through a network 13 so as to communicate therewith. The X-ray image captured by the mammography apparatus 10 is transmitted from the control device 12 to the image DB server 14 and is accumulated in the image DB server 14. The image DB server 14 is, for example, a picture archiving and communication system (PACS) server. The terminal apparatus 16 reads an X-ray image from the image DB server 14 and displays the X-ray image. The terminal apparatus 16 is used by, for example, a doctor to browse the X-ray image.

The apparatus main body 11 includes a stand 21 including a pedestal 21A and a support 21B that extends from the pedestal 21A in a height direction (Z direction) and a C-arm 22 which has a C-shape and is provided so as to be movable with respect to the support 21B.

The C-arm 22 comprises a radiation source accommodation portion 25 that accommodates an X-ray source 24, a detector accommodation portion 27 that accommodates an X-ray detector 26, and an arm portion 28 that integrally supports the radiation source accommodation portion 25 and the detector accommodation portion 27. The arm portion 28 is an example of a support portion. In the arm portion 28, the radiation source accommodation portion 25 is provided on the upper side in the height direction (Z direction) and the detector accommodation portion 27 is provided on the lower side in the height direction at a posture facing the radiation source accommodation portion 25.

The X-ray source 24 includes a plurality of X-ray tubes 36 and a housing 37 that accommodates the X-ray tubes 36. The X-ray source 24 is an example of a radiation source and the X-ray tube 36 is an example of a radiation tube. The X-ray source 24 selectively emits X-rays from each of the plurality of X-ray tubes 36 to the breast BR. In the radiation source accommodation portion 25, the plurality of X-ray tubes 36 are arranged in a row in the X direction. Here, one row means the arrangement state of the plurality of X-ray tubes 36 in the Z direction perpendicular to an imaging surface 26A of the X-ray detector 26, which will be described below, in a plan view.

The X-ray detector 26 detects the X-rays which have been emitted from each X-ray tube 36 and then transmitted through the breast BR and outputs an X-ray image of the breast BR. The X-ray detector 26 is an example of a radiation detector.

In the C-arm 22, a compression plate 29 is provided between the radiation source accommodation portion 25 and the detector accommodation portion 27. The compression plate 29 is supported by the arm portion 28 and is movable in the Z direction. The detector accommodation portion 27 functions as an imaging table on which the breast BR is placed. The compression plate 29 is moved to the detector accommodation portion 27, on which the breast BR has been placed, in the Z direction and compresses the breast BR interposed between the compression plate 29 and the detector accommodation portion 27. The compression plate 29 is made of a material transmitting X-rays such as plastic.

The C-arm 22 is connected to the support 21B through a connection portion 22A. The C-arm 22 is movable in the Z direction by the connection portion 22A. Therefore, the height of the C-arm 22 can be adjusted according to the height of the subject H. In addition, the C-arm 22 is provided so as to be rotatable on the Y-axis, which will be described below (see FIG. 5).

Here, the C-arm 22 is an example of an accommodation portion that accommodates the X-ray source 24 and the X-ray detector 26 at a posture where the X-ray source 24 and the X-ray detector 26 face each other. The stand 21 including the support 21B is an example of a base. The connection portion 22A connects the C-arm 22 to the support 21B such that the C-arm 22 is displaceable with respect to the support 21B. Therefore, the C-arm 22 is displaceable with respect to the support 21B while the relative positional relationship between the X-ray source 24 and the X-ray detector 26 is maintained.

A high voltage generation device 31 that generates a voltage to be applied to the X-ray source 24 is provided outside the C-arm 22, for example, in the support 21B. The high voltage generation device 31 is an example of a voltage generation device. A voltage cable 32 for supplying the voltage generated by the high voltage generation device 31 to the X-ray source 24 is connected to the high voltage generation device 31. The voltage cable 32 extends from the high voltage generation device 31 into the C-arm 22 through the support 21B and the connection portion 22A. The C-arm 22 is provided with a power distribution unit 61 which will be described below. The voltage cable 32 is connected to the power distribution unit 61. The voltage supplied from the voltage cable 32 is supplied to the X-ray source 24 through the power distribution unit 61.

Reference numeral 33 indicates a signal cable for transmitting a control signal from the control device 12 to the X-ray source 24. Similarly to the voltage cable 32, the signal cable 33 extends into the C-arm 22 through the support 21B and the connection portion 22A and is connected to the power distribution unit 61.

Reference numeral 23 indicates a face guard. The face guard 23 is made of an X-ray shielding member and shields X-rays to protect the face of the subject H from X-rays. The face guard 23 is attached, for example, to a lower part of the radiation source accommodation portion 25.

Figure 3:
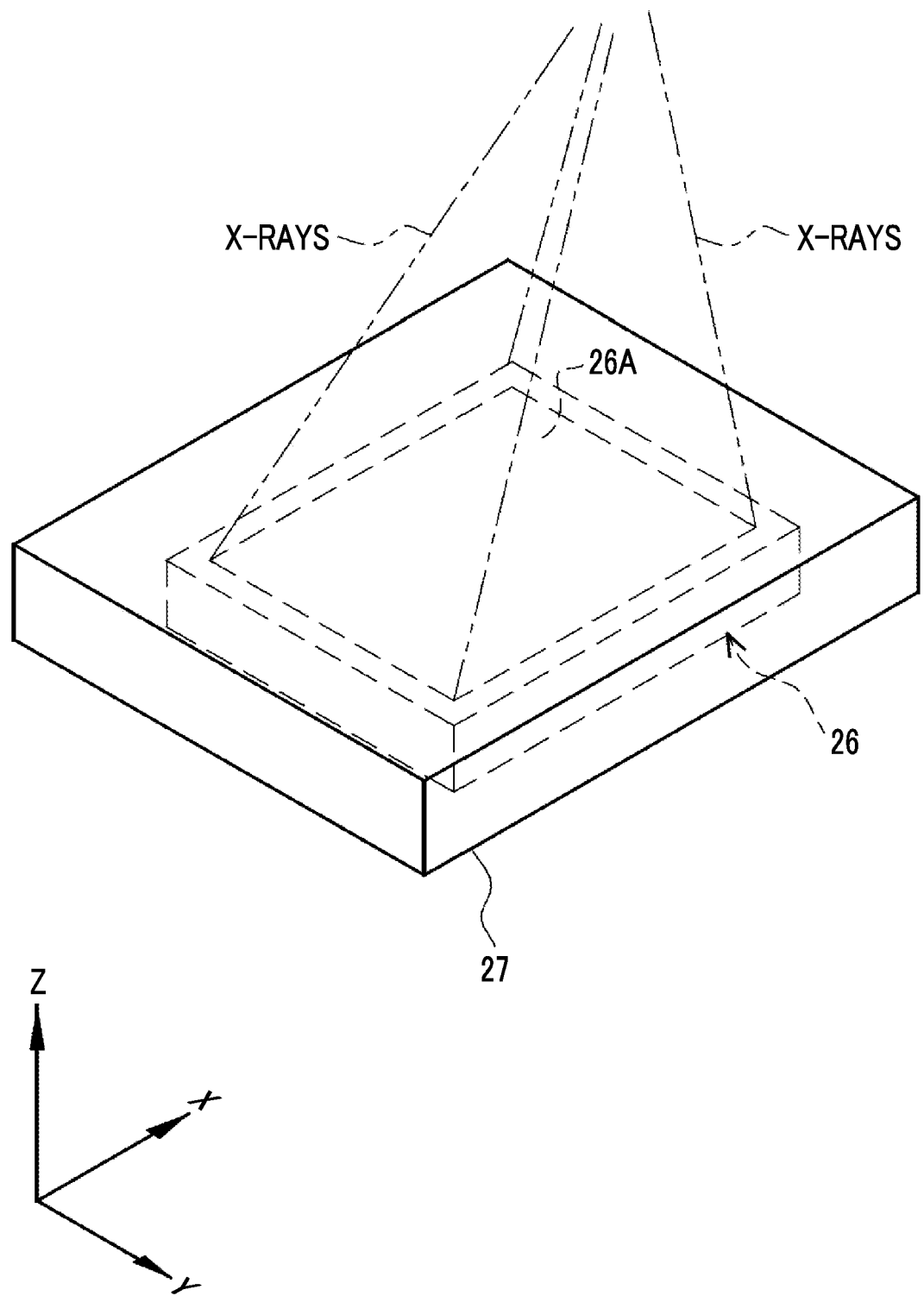
FIG. 3 is a diagram illustrating a detector accommodation portion and an X-ray detector.

As illustrated in FIG. 3, the X-ray detector 26 has an imaging surface 26A that detects the X-rays transmitted through the breast BR and captures a projection image which is an X-ray projection image of the breast BR. The imaging surface 26A is a two-dimensional plane in which pixels that convert X-rays into an electric signal are two-dimensionally arranged. The X-ray detector 26 is also referred to as a flat panel detector (FPD). The X-ray detector 26 may be an indirect conversion type that includes, for example, a scintillator converting X-rays into visible light and converts visible light emitted from the scintillator into an electric signal or a direct conversion type that directly converts X-rays into an electric signal.

In addition, for the relative position of each X-ray tube 36 with respect to the imaging surface 26A in the X direction, the center in the arrangement direction (X direction) of the X-ray tubes 36 is aligned with the center (see CP in FIG. 6) of the imaging surface 26A in the X direction. In addition, for the Y direction, in the mammography apparatus 10, the focus F (see FIG. 6) of each X-ray tube 36 is offset from the center of the imaging surface 26A in the Y direction to the front side (a side opposite to the support 21B) such that the chest wall of the breast BR is also irradiated with X-rays.

Figure 4:
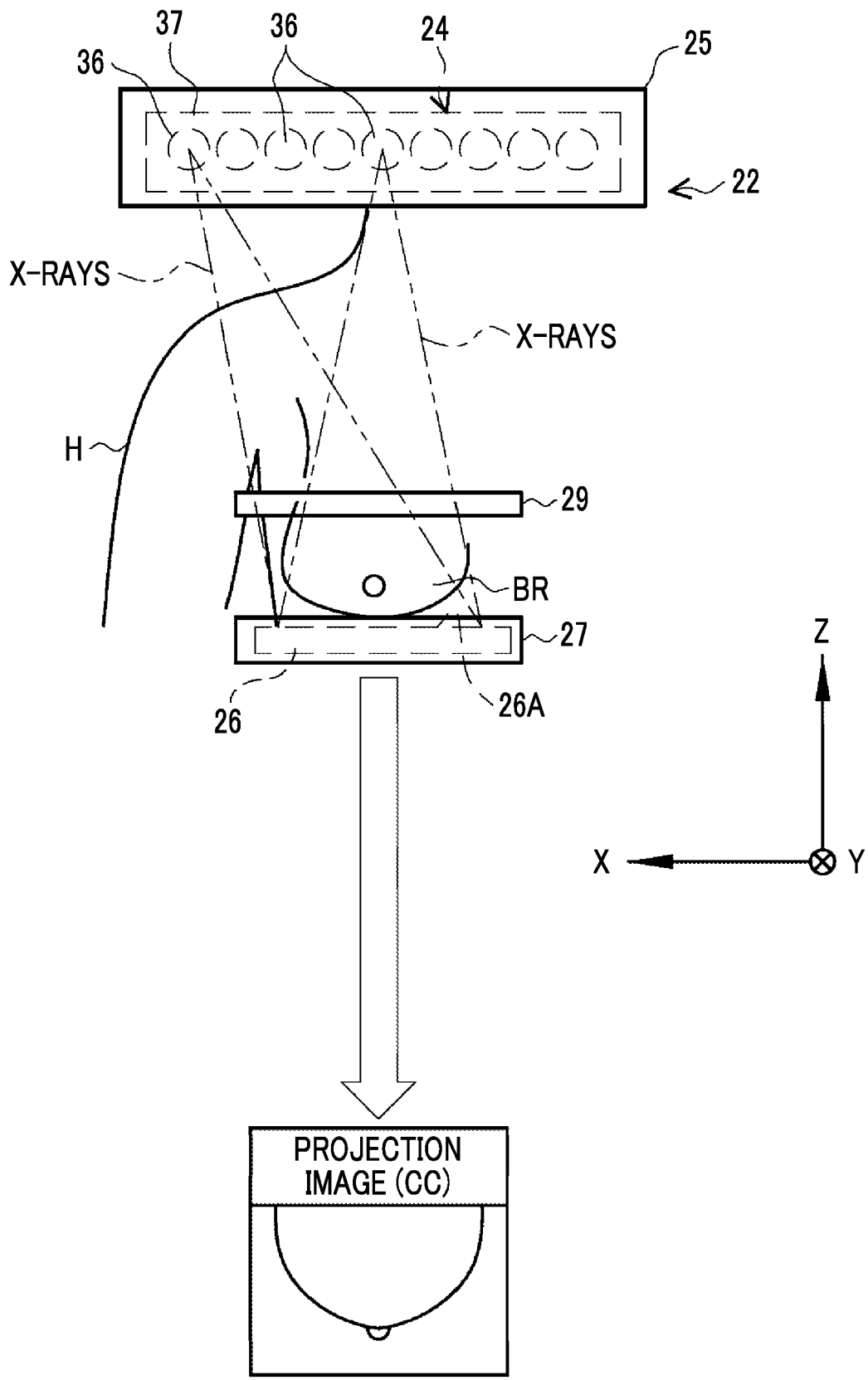
FIG. 4 is a diagram illustrating an aspect of CC imaging.
Figure 5:
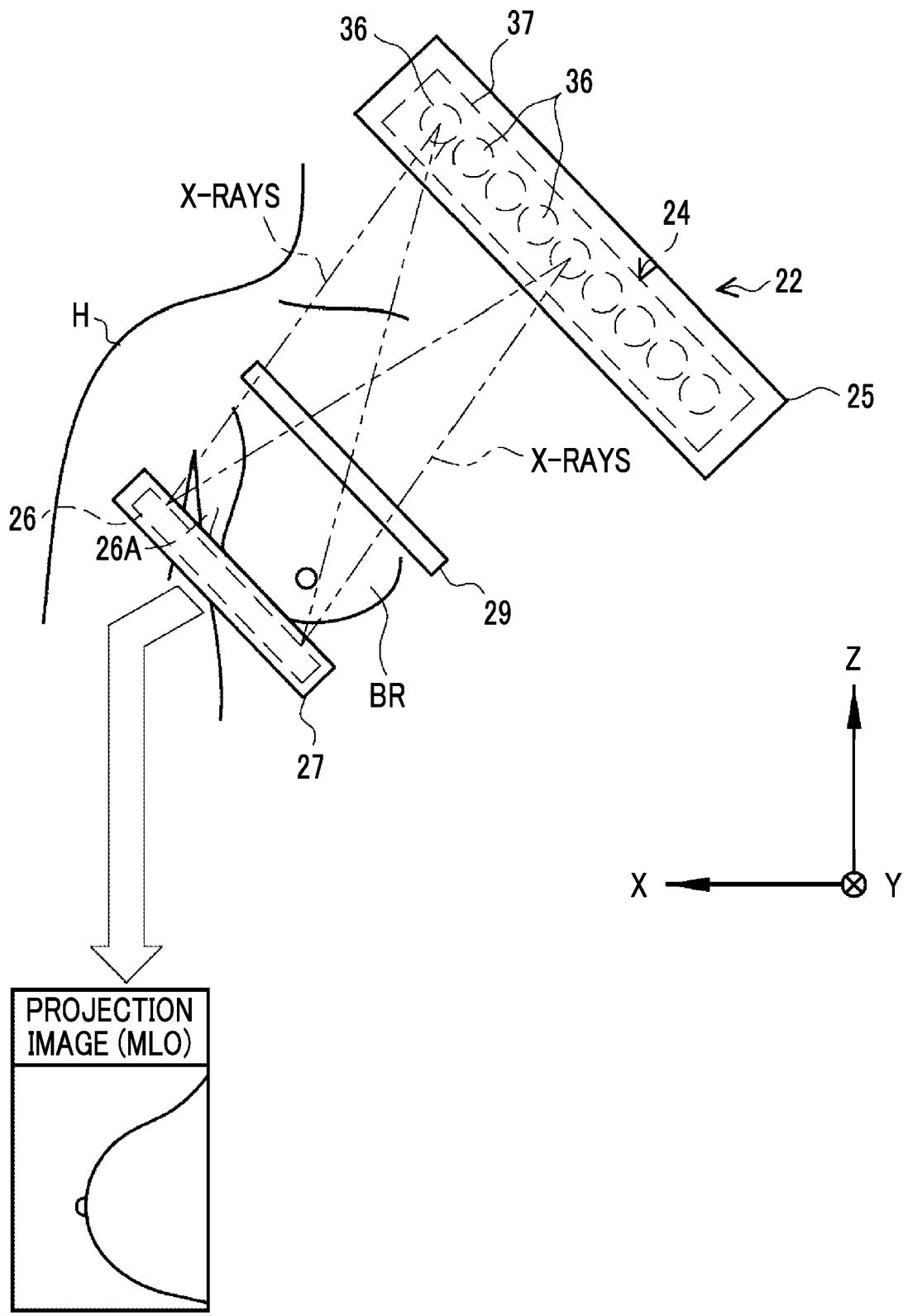
FIG. 5 is a diagram illustrating an aspect of MLO imaging.

As illustrated in FIGS. 4 and 5, the C-arm 22 is rotated on the Y-axis while the posture where the X-ray source 24 faces the imaging surface 26A of the X-ray detector 26 is maintained. Therefore, it is possible to perform imaging in two directions, such as craniocaudal view (CC) imaging illustrated in FIG. 4 and mediolateral oblique view (MLO) imaging illustrated in FIG. 5. The CC imaging is an imaging method which captures an image with the breast BR interposed in the vertical direction parallel to the Z direction and the MLO imaging is an imaging method which captures an image with the breast BR interposed in a direction that is inclined at an angle of about 60° with respect to the Z direction. In the CC imaging and the MLO imaging, a projection image (CC) and a projection image (MLO) captured in two different directions are obtained.

FIG. 4 illustrates the initial state of the C-arm 22. The imaging surface 26A is parallel to the X-Y plane. The imaging surface 26A and the X-ray source 24 face each other in the Z direction. In this example, the X direction, the Y direction, and the Z direction are used to define the imaging surface 26A and the arrangement direction of the plurality of X-ray tubes 36 in the C-arm 22. This definition is based on the premise that the C-arm 22 is in the initial state illustrated in FIG. 4. FIG. 5 illustrates a state in which the C-arm 22 is rotated on the Y-axis from the initial state. The arrangement direction of the plurality of X-ray tubes 36 is inclined with respect to the X direction. In the following description, it is premised that the C-arm 22 is in the initial state illustrated in FIG. 4 unless otherwise noted.

Figure 6:
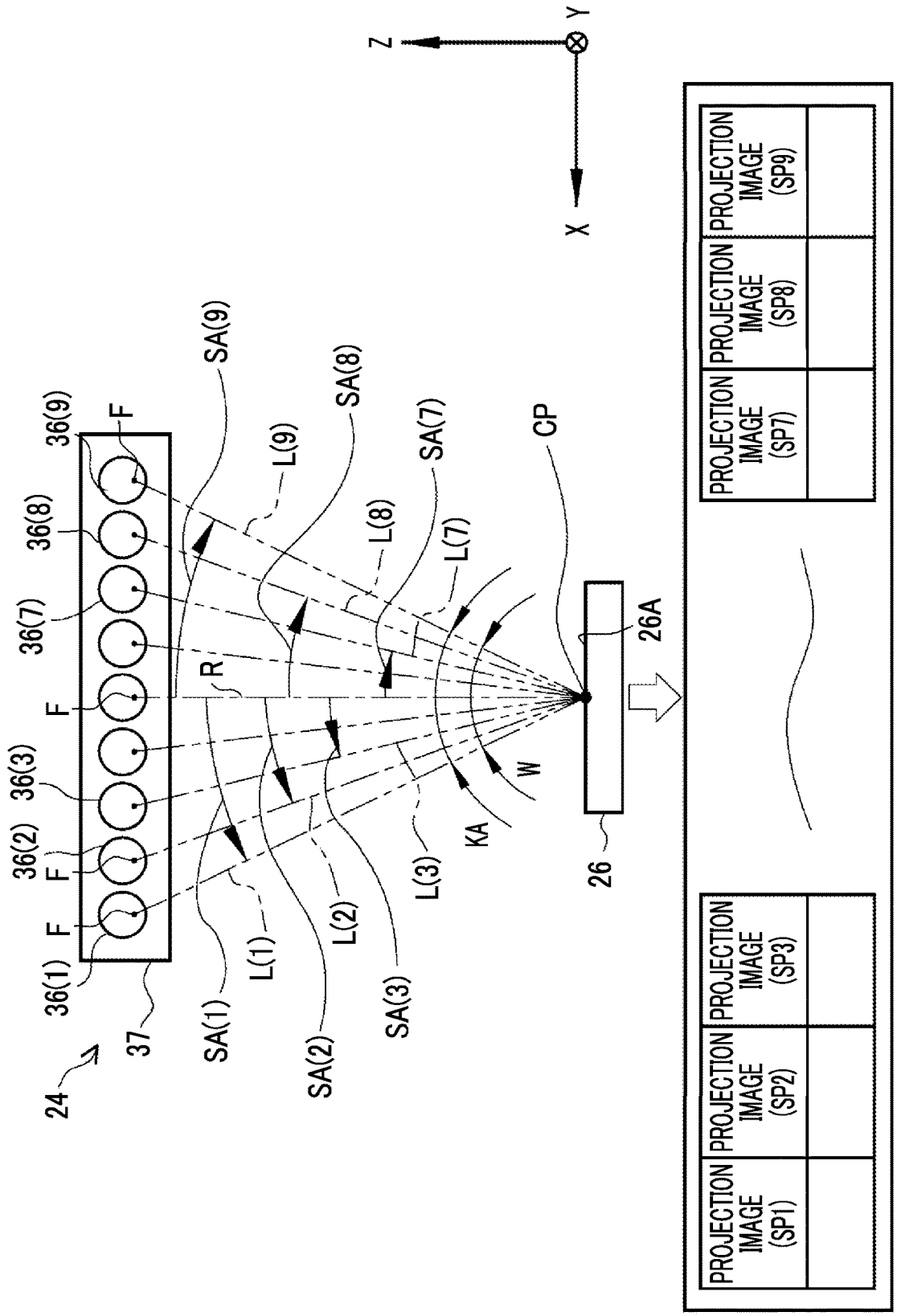
FIG. 6 is a diagram illustrating an aspect of tomosynthesis imaging.

As illustrated in FIG. 6 as an example, the X-ray source 24 includes, for example, nine X-ray tubes 36. The nine X-ray tubes 36 are linearly arranged along the X direction in the plane parallel to the imaging surface 26A.

The focus F of each of the nine X-ray tubes 36 is the focus at which X-rays are emitted in each X-ray tube 36 and is the irradiation position of each X-ray tube 36. Therefore, the irradiation angles SA of the nine X-ray tubes 36 with respect to the imaging surface 26A are different from each other. Here, the irradiation angle SA means an angle formed between a normal line R (also see FIG. 3) to the imaging surface 26A which extends from the center CP (also see FIG. 3) of the imaging surface 26A in the X direction and a segment L connecting the focus F which is the irradiation position of each X-ray tube 36 and the center CP in the X-Z plane.

In the tomosynthesis imaging, it is necessary to acquire a plurality of projection images SP with different X-ray irradiation angles SA. Since the mammography apparatus 10 includes the plurality of X-ray tubes 36 with different irradiation angles SA, the mammography apparatus 10 can acquire the projection images SP with different irradiation angles SA even in a state in which the plurality of X-ray tubes 36 are fixed.

In FIG. 6, in order to distinguish, for example, the X-ray tubes 36 and the irradiation angles SA of the X-ray tubes 36, parenthesized numbers (1) to (9) are given such that an X-ray tube 36 disposed at the left end which is one end in the arrangement direction is the first X-ray tube 36 and an X-ray tube 36 disposed at the other end is the ninth X-ray tube 36. The irradiation angle SA(1) of the X-ray tube 36(1) disposed at the left end is an angle formed between the normal line R and a segment L(1) connecting the focus F of the X-ray tube 36(1) and the center CP of the imaging surface 26A. The irradiation angle SA(2) of the second X-ray tube 36(2) from the left side is an angle formed between the normal line R and a segment L(2) connecting the focus F of the X-ray tube 36(2) and the center CP of the imaging surface 26A. The irradiation angle SA(1) of the first X-ray tube 36(1) is larger than the irradiation angle SA(2) of the second X-ray tube 36(2).

Similarly, the irradiation angle SA(9) of the X-ray tube 36(9) disposed at the right end is an angle formed between the normal line R and a segment L(9) connecting the focus F of the X-ray tube 36(9) and the center CP of the imaging surface 26A. The irradiation angle SA(8) of the second X-ray tube 36(8) from the right side is an angle formed between the normal line R and a segment L(8) connecting the focus F of the X-ray tube 36(8) and the center CP of the imaging surface 26A. The irradiation angle SA(9) of the ninth X-ray tube 36(9) is larger than the irradiation angle SA(8) of the eighth X-ray tube 36(8). In a case in which the X-ray tubes 36 are linearly arranged along the X direction in the plane parallel to the imaging surface 26A as in this example, as the position of each X-ray tube 36 becomes further away from the center CP, the irradiation angle SA of the X-ray tube 36 becomes larger.

In addition, reference numeral W indicates an angle formed between the segments L corresponding to the X-ray tubes 36 at both ends in the X-ray source 24 and means a spread angle in the arrangement direction (X direction) of the plurality of X-ray tubes 36 in the X-ray source 24. In this example, the spread angle W is the angle formed between the segment L(1) corresponding to the X-ray tube 36(1) at the left end and the segment L(9) corresponding to the X-ray tube 36(9) at the right end.

One tomosynthesis imaging operation of the mammography apparatus 10 means an operation of selectively emitting X-rays from the plurality of X-ray tubes 36 and acquiring a plurality of projection images SP based on the emission of the X-rays from each selected X-ray tube 36. The plurality of projection images SP have different irradiation angles SA. FIG. 6 illustrates an aspect in which nine projection images SP, that is, projection images SP1 to SP9 are acquired.

Reference numeral KA indicates a scanning angle in a case in which tomosynthesis imaging is performed. Here, the scanning angle KA means the sum of the absolute values of the maximum irradiation angles SA in the positive direction (clockwise direction) and the negative direction (counterclockwise direction) from the normal line R among a plurality of irradiation angles SA corresponding to a plurality of projection images SP acquired by one tomosynthesis imaging operation.

In some cases, the scanning angle KA is set to be smaller than the spread angle W illustrated in FIG. 6. In a case in which a movement mechanism for moving the X-ray source 24 in the X direction is provided, it is possible to set the scanning angle KA to be greater than the spread angle W. In a case in which the X-ray source 24 is fixed, the spread angle W illustrated in FIG. 6 becomes the maximum value of the scanning angle KA.

As the scanning angle KA becomes larger, the projection image SP with a larger irradiation angle SA is obtained. As the scanning angle KA becomes larger, depth resolution becomes higher. Therefore, it is possible to create a tomographic image in which the overlap or lesion structure of the mammary glands is clearly separated. In addition, since the irradiation angle SA of X-rays becomes smaller as the scanning angle KA becomes smaller, a region that can be captured as an image in the entire breast BR is large. The scanning angle KA is set according to the purpose of imaging. The scanning angle KA is set in the range of, for example, 15° to 60°.

Figure 7:
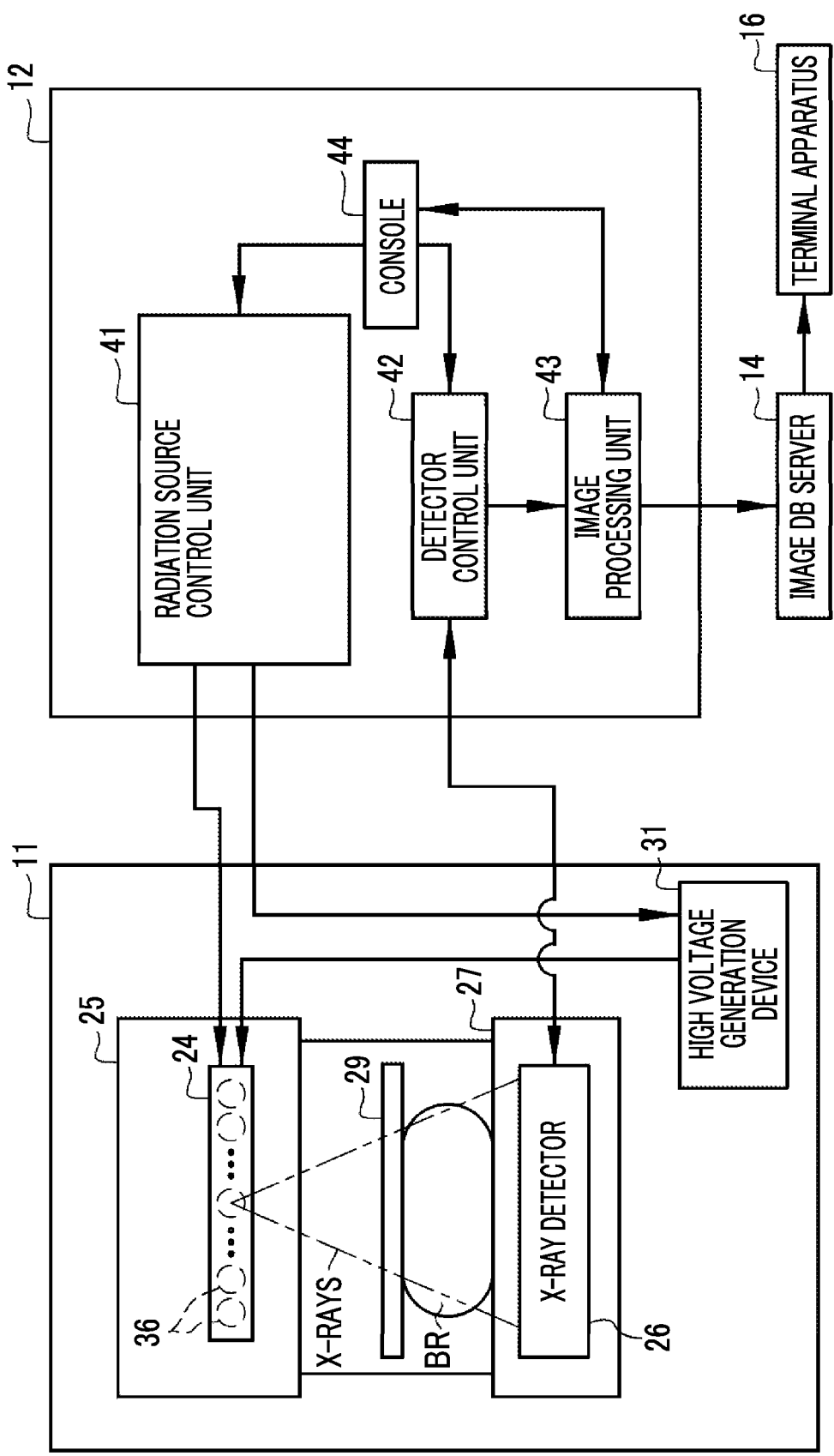
FIG. 7 is a block diagram schematically illustrating an electrical configuration of the mammography apparatus.

As illustrated in FIG. 7, the control device 12 controls each unit of the apparatus main body 11. The control device 12 comprises a radiation source control unit 41, a detector control unit 42, an image processing unit 43, and a console 44.

The radiation source control unit 41 controls the irradiation conditions of the X-ray source 24 and the irradiation timing and irradiation order of each X-ray tube 36. For example, the irradiation conditions include the tube voltage, tube current, and irradiation time of the X-ray tube 36 and are set according to the size of the breast BR and the purpose of imaging. The tube voltage defines the energy of X-rays, and the tube current and the irradiation time define the cumulative amount of X-rays. The tube voltage is set through the high voltage generation device 31.

The detector control unit 42 performs synchronization control which directs the X-ray detector 26 to start an imaging operation in synchronization with the start timing of a preparation operation, such as a reset process of the X-ray detector 26, and the irradiation timing of the X-ray source 24. In addition, the detector control unit 42 acquires the projection image SP from the X-ray detector 26.

The image processing unit 43 performs image processing, such as frequency processing, a noise filtering process, and a dynamic range adjustment process, for the projection image SP acquired from the detector control unit 42. The image processing unit 43 reconstructs a tomographic image including a structure of any tomographic plane of the breast BR on the basis of a plurality of projection images SP with different irradiation angles SA, in addition to the above-mentioned general image processing.

Figure 8:
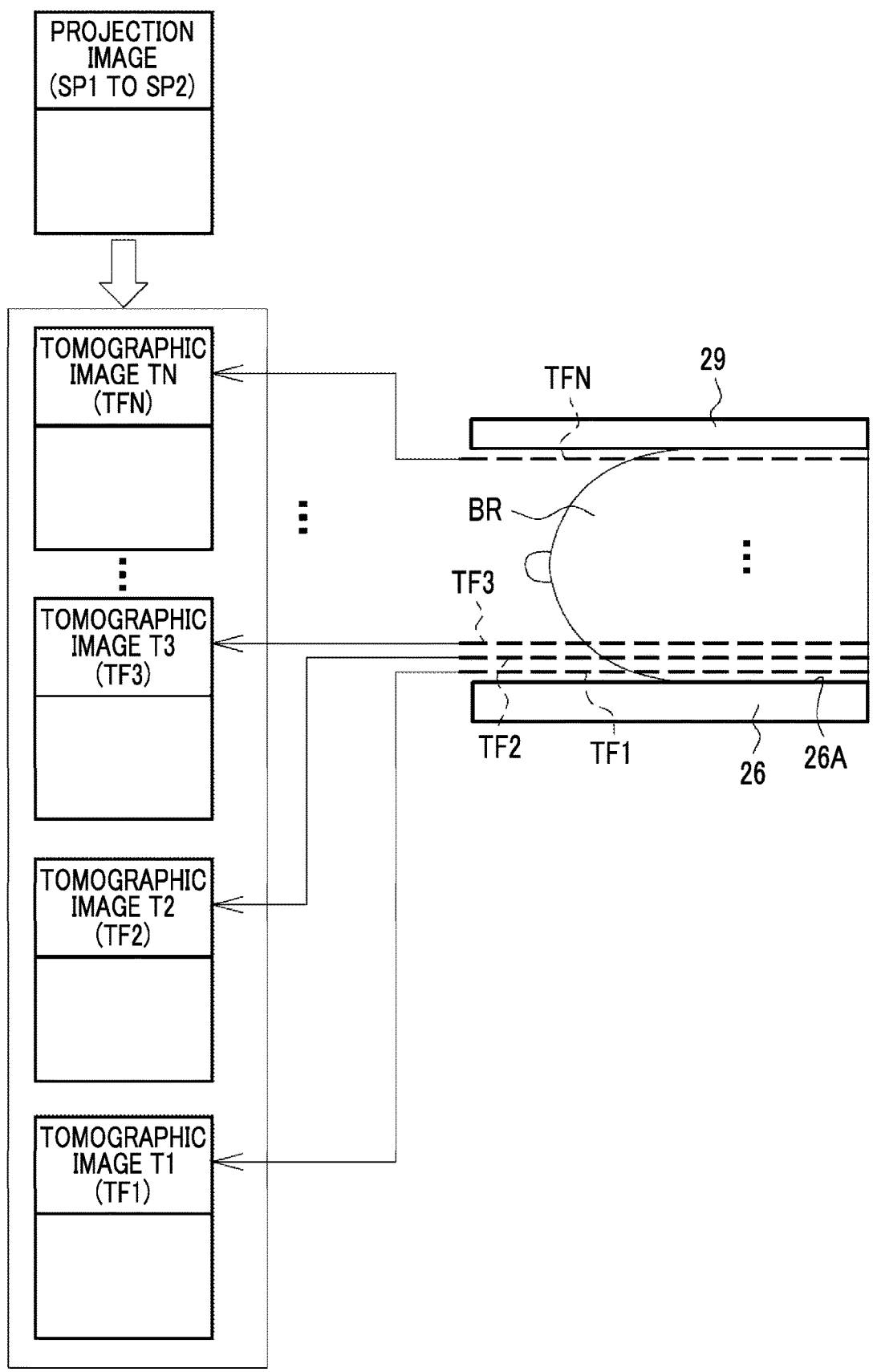
FIG. 8 is a diagram illustrating a tomographic image.

As illustrated in FIG. 8, the image processing unit 43 generates tomographic images T1 to TN corresponding to any tomographic planes TF1 to TFN of the breast BR from the plurality of projection images SP, using a known method such as a filtered back projection (FBP) method or a shift-and-add method. The tomographic plane TF is a plane parallel to the imaging surface 26A of the X-ray detector 26. In the tomographic images T1 to TN, images in which structures in the tomographic planes TF1 to TFN of the breast BR have been highlighted are obtained.

The image processing unit 43 reconstructs the tomographic images T1 to TN considering the irradiation angle SA of each of the plurality of projection images SP. In the reconstruction process, calculation is simplified in a case in which there is regularity in the irradiation angle SA of each projection image SP, for example, in a case in which the difference between the irradiation angles SA of the projection images SP is uniform. However, even though there is no regularity in the irradiation angle SA, it is possible to perform the reconstruction in a case in which the irradiation angle SA is known.

In FIG. 7, the console 44 is an operation terminal that is used by a medical staff, such as a radiology technical or a doctor, to operate the mammography apparatus 10. The console 44 has an imaging condition setting function and a function of displaying the X-ray image acquired by the X-ray detector 26 on a display such that the X-ray image is checked. The imaging conditions include, for example, the scanning angle KA in a case in which tomosynthesis imaging is performed in addition to the irradiation conditions of the X-ray source 24.

Figure 9:
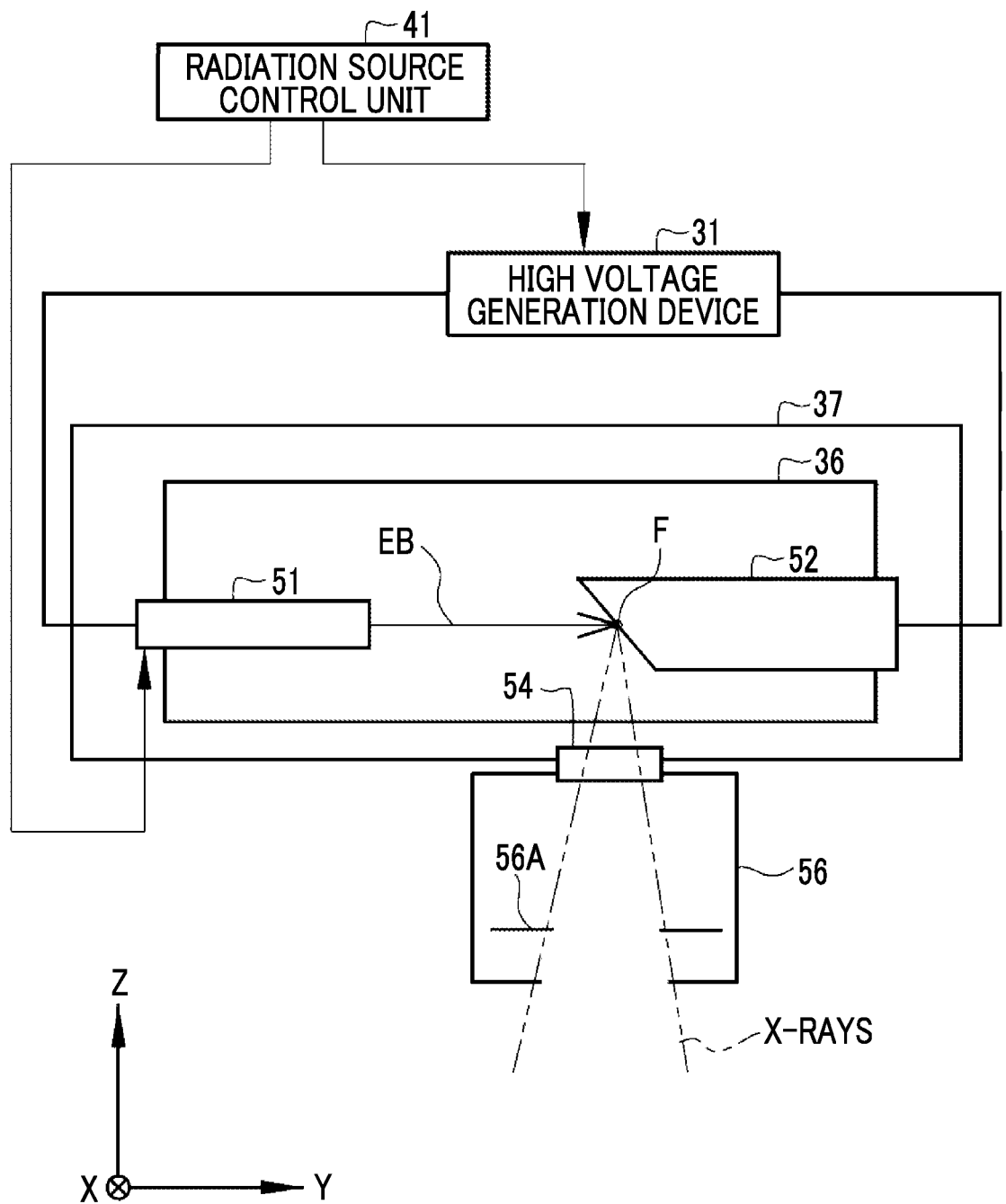
FIG. 9 is a diagram illustrating a configuration of an X-ray tube.

As illustrated in FIG. 9, the X-ray tube 36 comprises a cathode 51 and an anode 52. The cathode 51 and the anode 52 are accommodated in a vacuum glass container with a substantially cylindrical shape. The cathode 51 is an electron emission source that emits electrons EB to the anode 52. The anode 52 is a target with which the electrons EB emitted from the cathode 51 collide. For example, tungsten or molybdenum is used as the material forming the anode 52. The X-ray tube 36 according to this example is a fixed anode type in which a fixed anode is used as the anode 52. The fixed anode means a type without a rotating structure for rotating a disk-shaped anode, unlike a rotating anode type.

The cathode 51 and the anode 52 are electrically connected to the high voltage generation device 31. The radiation source control unit 41 controls the high voltage generation device 31 such that a high voltage is applied between the cathode 51 and the anode 52. The cathode 51 in this example is a cold cathode type which will be described below. The radiation source control unit 41 and the cathode 51 are connected by a control signal line. The radiation source control unit 41 controls a gate voltage applied to a gate electrode 51B, which will be described below, through the control signal line in a state in which a high voltage is applied between the cathode 51 and the anode 52. The emission of the electrons EB from the cathode 51 is controlled by the control of the gate voltage. In a case in which the electrons EB emitted from the cathode 51 collide with the anode 52, X-rays are emitted from the focus F where the electrons EB have collided.

The X-ray tube 36 is accommodated in the housing 37 filled with insulating oil. The housing 37 is provided with an X-ray transmission window 54. The X-ray transmission window 54 is made of a material transmitting X-rays and emits X-rays to the outside of the housing 37 while sealing the inside of the housing 37. An irradiation field limiter 56 (also referred to as a collimator) which limits the irradiation field of X-rays in the breast BR is provided on the front surface of the X-ray transmission window 54. The X-rays emitted from the X-ray transmission window 54 are incident on the irradiation field limiter 56. The irradiation field limiter 56 includes a plurality of shielding plates 56A that shield X-rays. The plurality of shielding plates 56A define, for example, a rectangular irradiation opening. The plurality of shielding plates 56A are moved to adjust the size of the irradiation opening.

Figure 10:
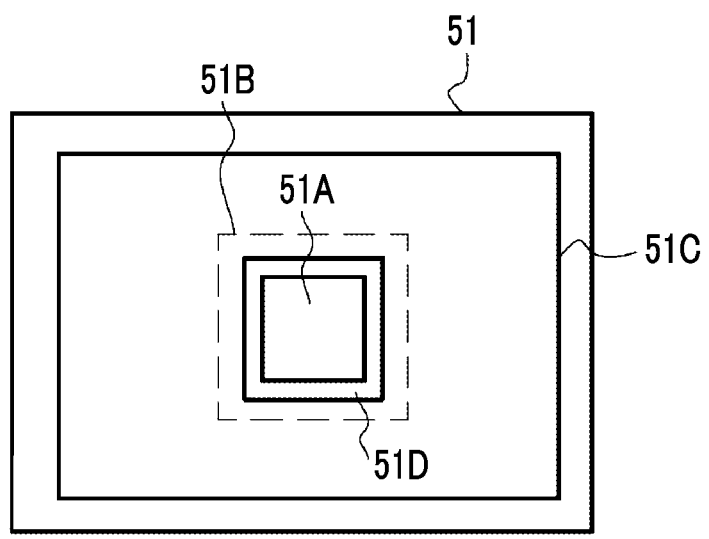
FIG. 10 is a diagram illustrating an electron emission area of a cathode.

As illustrated in FIG. 10, the cathode 51 according to this example is a cold cathode type, specifically, a field emission type which emits electron beams using a field emission phenomenon that occurs in a case in which the electric field is applied to the surface of a conductor. The diameter of the X-ray tube 36 is, for example, equal to or less than about 50 mm.

The cathode 51 of the field emission type has, for example, a structure in which an emitter electrode 51A and a gate electrode 51B are provided on a semiconductor substrate 51C made of crystalline silicon. The emitter electrode 51A is obtained by, for example, forming a carbon nanotube in a conical shape. The emitter electrode 51A functions as an electron emission area which emits the electrons EB.

The gate electrode 51B is connected to the emitter electrode 51A. As described above, in a case in which X-rays are emitted, the radiation source control unit 41 controls the high voltage generation device 31 such that a high voltage is applied between the cathode 51 and the anode 52. In this state, the radiation source control unit 41 applies a gate voltage to the gate electrode 51B. In a case in which the gate voltage is applied to the gate electrode 51B, the electrons EB are emitted from the emitter electrode 51A.

In addition, a focusing electrode 51D is provided around the emitter electrode 51A. In a case in which a focusing voltage is applied to the focusing electrode, the electrons EB emitted from the emitter electrode 51A are accelerated toward the anode 52 and a beam of the electrons EB is focused.

Figure 11:
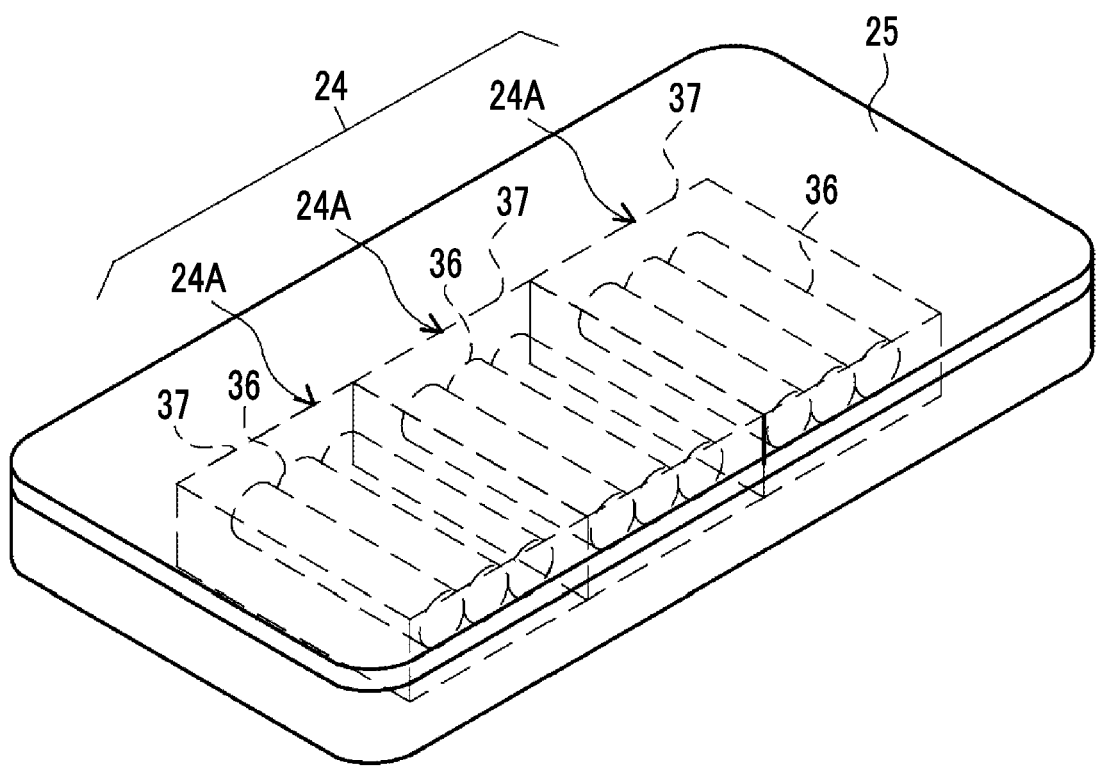
FIG. 11 is an enlarged view illustrating a radiation source accommodation portion and an X-ray source.

As described in detail in FIG. 11, the X-ray source 24 includes a plurality of units 24A in which the plurality of X-ray tubes 36 are divided and accommodated. Each unit 24A includes the X-ray tubes 36 and the housing 37 accommodating the X-ray tubes 36. In this example, three units 24A are provided and three housings 37 whose number is equal to the number of units 24A are provided. Three X-ray tubes 36 are accommodated in each unit 24A. That is, each unit 24A according to this example includes three X-ray tubes 36 and the housing 37 accommodating the three X-ray tubes 36.

Figure 12:
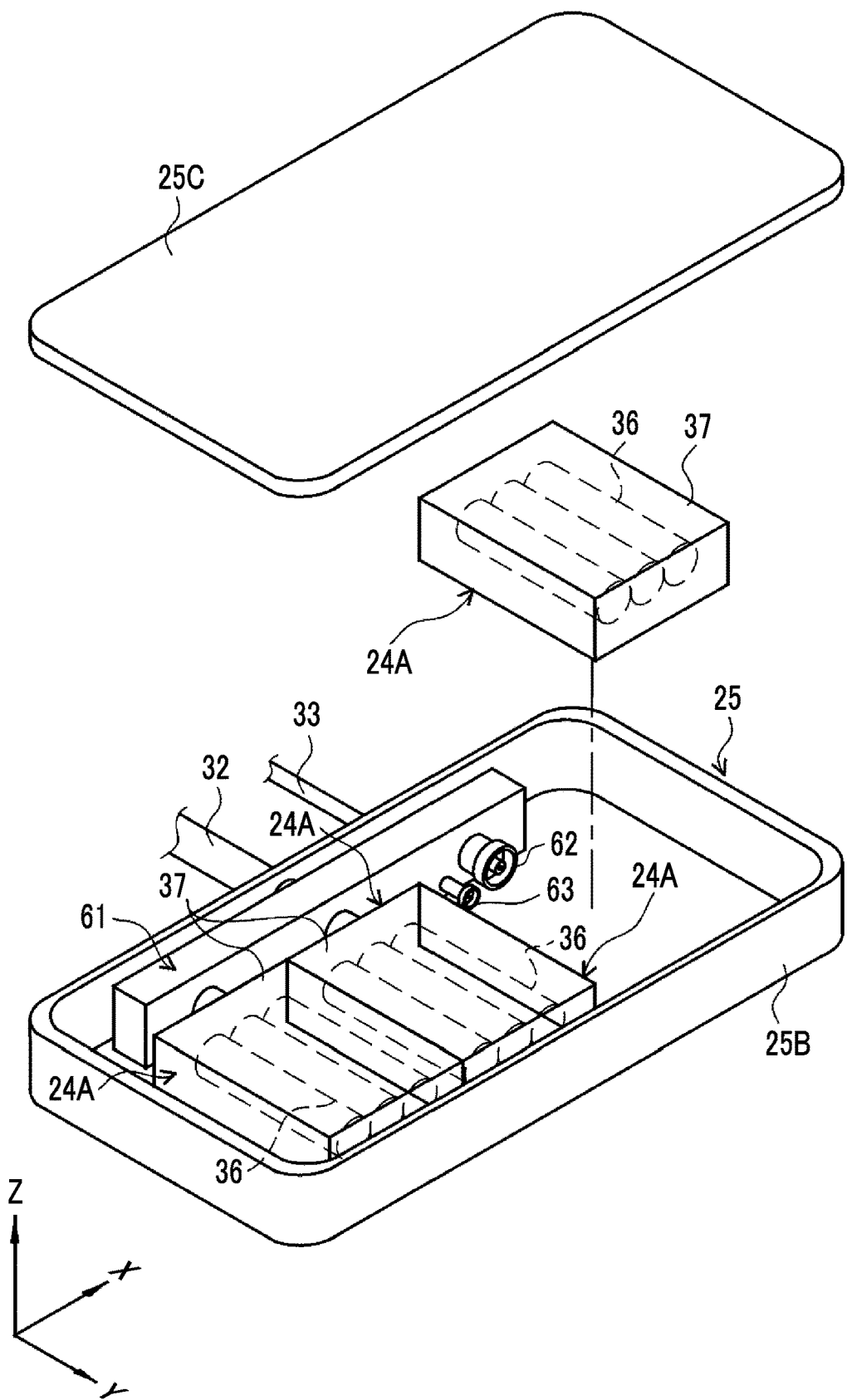
FIG. 12 is a diagram illustrating the radiation source accommodation portion with a cover open.

As illustrated in FIG. 12, the radiation source accommodation portion 25 includes an accommodation portion main body 25B and a cover 25C. The cover 25C is attachable to and detachable from the accommodation portion main body 25B. The cover 25C is detached such that each unit 24A in the radiation source accommodation portion 25 can be replaced.

In addition, a power distribution unit 61 is provided in the radiation source accommodation portion 25. The power distribution unit 61 is an example of a distribution unit that is provided in the radiation source accommodation portion 25 which is a part of the C-arm 22 as an example of the accommodation portion and distributes a voltage supplied through a voltage cable 32 to each unit 24A of the X-ray source 24. The voltage cable 32 is connected to the power distribution unit 61.

Figure 13:
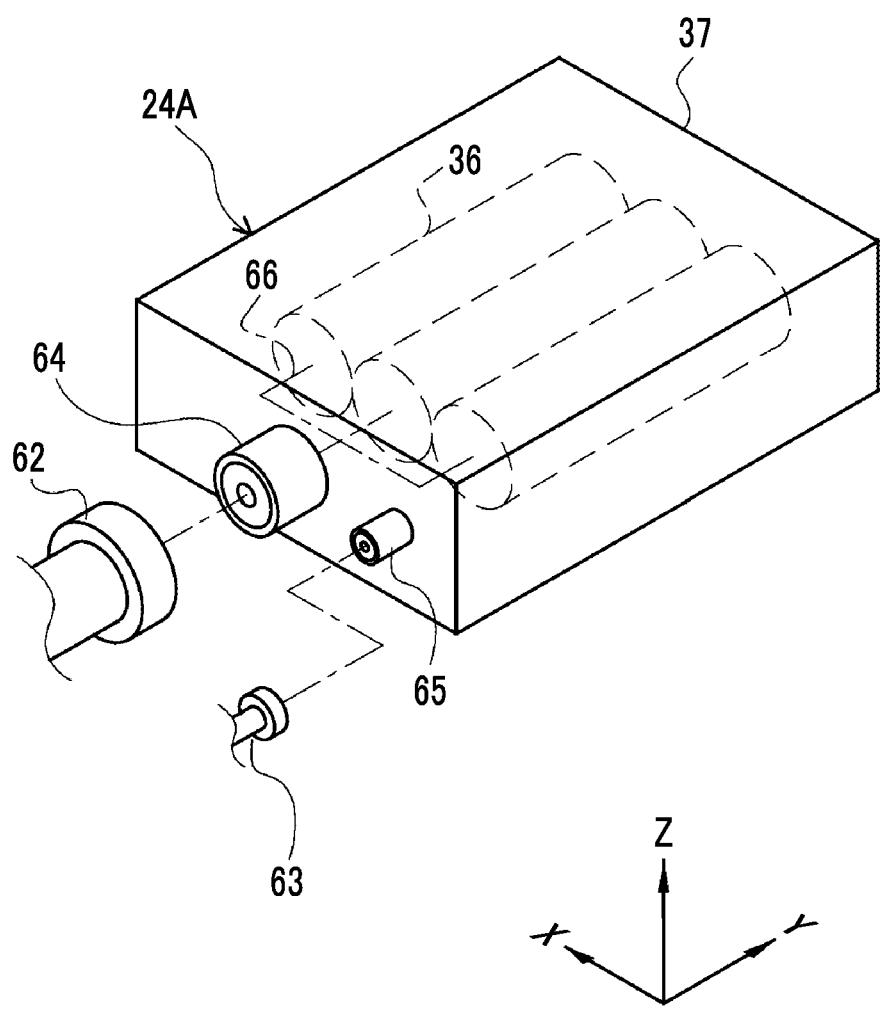
FIG. 13 is a diagram illustrating a connector of a unit of the X-ray source.
Figure 14:
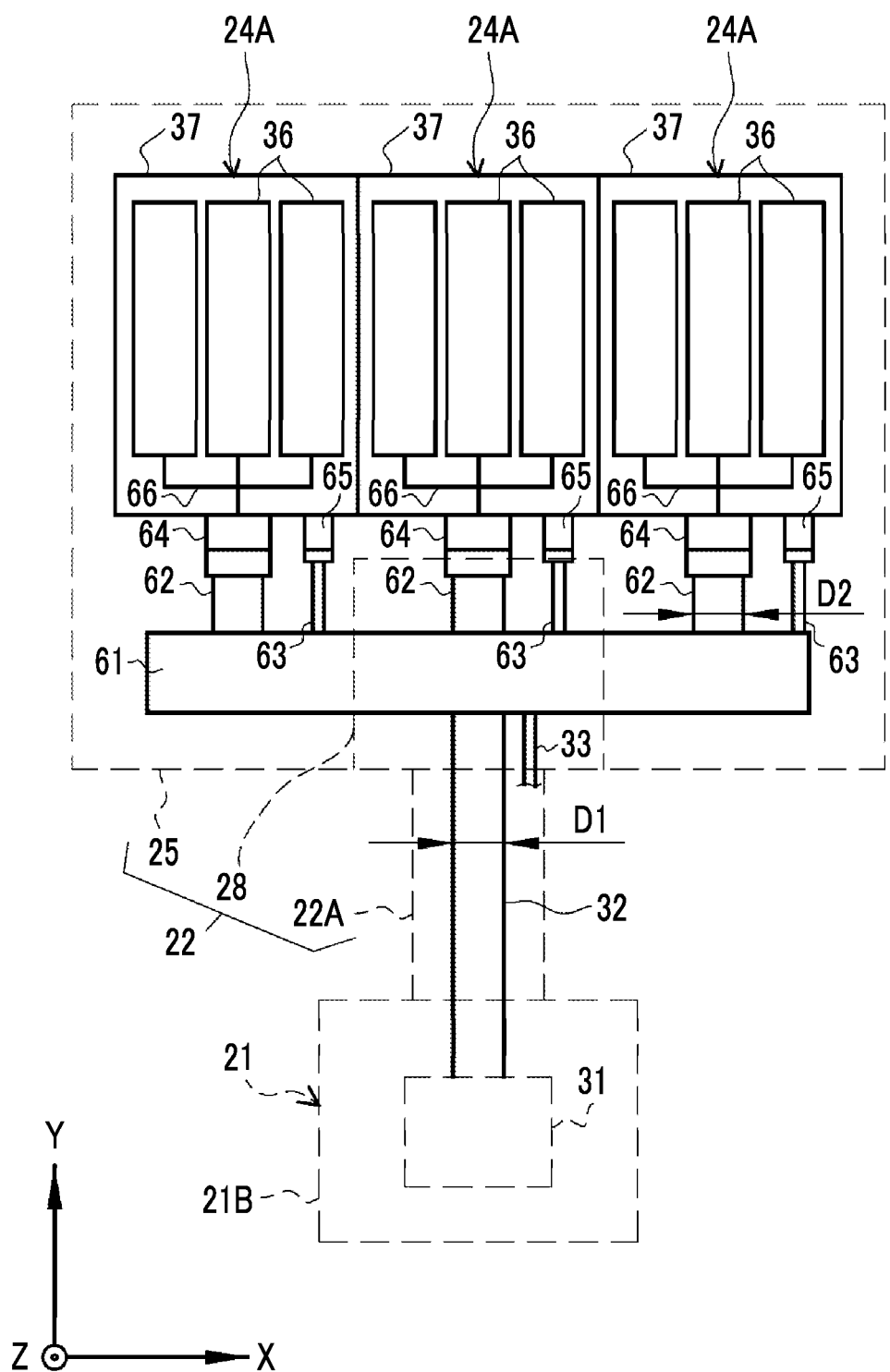
FIG. 14 is a diagram illustrating a distribution method using a power distribution unit.

As illustrated in FIGS. 13 and 14, the power distribution unit 61 is provided with three voltage connector cables 62 which correspond to three units 24A and are used for connection to each unit 24A. As illustrated in FIG. 13, each unit 24A is provided with a voltage connector 64. As illustrated in FIG. 14, each voltage connector cable 62 of the power distribution unit 61 is connected to each voltage connector 64 of each unit 24A. The voltage supplied from the voltage cable 32 is supplied to each unit 24A through each voltage connector cable 62 and each voltage connector 64.

In each unit 24A, the voltage connector 64 and each X-ray tube 36 are connected to each other by a wiring line 66. The voltage supplied from the voltage cable 32 is finally applied to the cathode 51 and the anode 52 of each X-ray tube 36 through the wiring lines 66.

In addition, a signal cable 33 is connected to the power distribution unit 61. Three signal connector cables 63 which correspond to three units 24A and are used for connection to each unit 24A are provided in the power distribution unit 61. As illustrated in FIG. 13, a signal connector 65 is provided in each unit 24A. As illustrated in FIG. 14, each signal connector cable 63 of the power distribution unit 61 is connected to each signal connector 65 of each unit 24A. A control signal transmitted through the signal cable 33 is transmitted to each unit 24A through each signal connector cable 63 and each signal connector 65.

In addition, in each unit 24A, the signal connector 65 and each X-ray tube 36 are connected to each other by a wiring line (not illustrated) and the control signal from the signal cable 33 is transmitted to each X-ray tube 36 through the wiring line. The control signal is, for example, a control signal for applying a gate voltage to the gate electrode 51B of the cathode 51. The irradiation timing and the irradiation time of each X-ray tube 36 are controlled by the control signal.

As illustrated in FIG. 14, the voltage cable 32 is significantly thicker than the signal cable 33. The reason is that, since a high voltage is applied through the voltage cable 32, it is necessary to thicken an insulating covering material in the voltage cable 32. An increase in the diameter of the voltage cable 32 is caused by the thickness of the covering material. Therefore, even in a case in which the voltage cable 32 is branched, the diameter of a branched portion does not change. For example, as illustrated in FIG. 14, a cable portion of each voltage connector cable 62 of the power distribution unit 61 is the same cable as the voltage cable 32. A diameter D2 of the cable portion is almost equal to a diameter D1 of the voltage cable 32. The reason is that, in the voltage connector cable 62 after branching, it is also necessary to thicken an insulating covering material as in the voltage cable 32 before branching.

In contrast, the diameter of the wiring line 66 in each unit 24A is less than the diameter D1 of the voltage cable 32. The reason is that the inside of the housing 37 of each unit 24A is filled with insulating oil and insulation measures are taken.

The operation of the above-mentioned structure has been described above. In a case in which tomosynthesis imaging is performed by the mammography apparatus 10, first, imaging conditions are set to the mammography apparatus 10 through the console 44. The imaging conditions include, for example, the scanning angle KA in addition to the X-ray irradiation conditions. The irradiation conditions are set according to, for example, the thickness of the object (breast BR).

Then, the breast BR of the subject H is placed on the detector accommodation portion 27 which functions as an imaging table. Then, the breast BR is compressed by the compression plate 29 and is positioned. Then, in a case in which an operation command to start imaging is input through the console 44, tomosynthesis imaging is started. The radiation source control unit 41 commands the high voltage generation device 31 to supply a voltage. The voltage generated by the high voltage generation device 31 is supplied to the power distribution unit 61 through the voltage cable 32. The power distribution unit 61 distributes the voltage to each unit 24A through the voltage connector cables 62. The voltage is applied to each X-ray tube 36 through the wiring lines 66.

The control signal issued by the radiation source control unit 41 is transmitted to each X-ray tube 36 through the signal cable 33 and the power distribution unit 61. The radiation source control unit 41 sequentially transmits the control signals to the plurality of X-ray tubes 36 selected according to the scanning angle KA from the X-ray tube 36 at the end in the arrangement direction. Therefore, X-rays are sequentially emitted from the plurality of X-ray tubes 36 with different irradiation angles SA. Then, the X-ray detector 26 acquires a plurality of projection images SP of the breast BR which correspond to the focuses F of the X-ray tubes 36. Then, the mammography apparatus 10 ends one tomosynthesis imaging operation.

As described above, since the X-ray source 24 of the mammography apparatus 10 according to this example includes the plurality of units 24A in which the plurality of X-ray tubes 36 are divided and accommodated, the deterioration of maintenance is suppressed. That is, in a case in which there is a broken X-ray tube 36, the broken X-ray tube 36 is replaced. In a case in which the broken X-ray tube 36 is replaced, it is not necessary to replace all of the X-ray tubes 36 since the X-ray source 24 includes the plurality of units 24A and it is sufficient to replace only the unit 24A accommodating the broken X-ray tube 36.

In a case in which the X-ray tube 36 is replaced, it is necessary to adjust the focal position and output of the replaced X-ray tube 36. In the mammography apparatus 10 according to this example, since each unit 24A can be replaced, it is not necessary to adjust the focal position and output of all of the X-ray tubes 36 and it is sufficient to adjust the focal position and output of the replaced unit 24A. Therefore, it is possible to suppress the complexity of a maintenance operation. In addition, in a case in which all of the X-ray tubes 36 including the X-ray tube 36 which has not been broken need to be replaced, there is a concern that the cost of parts will increase and a maintenance cost will be high. However, in this example, since each unit 24A can be replaced, an increase in the maintenance cost is also suppressed.

As such, according to the mammography apparatus 10 of this example, it is possible to suppress the deterioration of maintenance in a case in which a plurality of X-ray tubes 36 are provided.

As in the mammography apparatus 10 according to this example, in a case in which a tomosynthesis imaging function is provided, since a plurality of X-ray tubes 36 with different irradiation angles are provided, the effect of reducing the imaging time of one tomosynthesis imaging operation as compared to the related art in which tomosynthesis imaging is performed while one X-ray tube is being moved is obtained.

In addition, the plurality of X-ray tubes 36 are arranged in a row. Therefore, the same tomographic image reconstruction calculation as that in the related art in which one X-ray tube 36 is moved in one direction is performed. As a result, the calculation process is simplified.

The mammography apparatus 10 according to this example includes the connection portion 22A that connects the C-arm 22 accommodating the X-ray source 24 and the X-ray detector 25 to the support 21B such that the C-arm 22 is displaceable with respect to the support 21B. The voltage cable 32 extending from the high voltage generation device 31 which is provided outside the C-arm 22 is inserted into the connection portion 22A. The voltage cable 32 extends into the C-arm 22 through the connection portion 22A. The power distribution unit 61 that distributes the voltage supplied through the voltage cable 32 to each of the plurality of units 24A of the X-ray source 24 is provided in the radiation source accommodation portion 25 of the C-arm 22.

Since the power distribution unit 61 is provided in the C-arm 22 accommodating the X-ray source 24, it is sufficient to insert one voltage cable 32 into the connection portion 22A even in a case in which the X-ray source 24 includes the plurality of units 24A.

In a case in which a distribution unit, such as the power distribution unit 61, is not provided in the C-arm 22, the voltage cables 32 corresponding to the plurality of units 24A need to be inserted into the connection portion 22A. As described above, the diameter of the voltage cable 32 is large. Therefore, in a case in which the plurality of the voltage cables 32 are inserted, a cable insertion duct in the connection portion 22A becomes very large. In addition, a movable component, such as a shaft, for displacing the C-arm 22 is provided in the connection portion 22A. Therefore, in a case in which the number of voltage cables 32 increases, the concern of the interference between the movable component in the connection portion 22A and the voltage cables 32 also increases.

Therefore, the configuration in which a distribution unit, such as the power distribution unit 61, is provided in the C-arm 22 accommodating the X-ray source 24 makes it possible to suppress an increase in the diameter of the cable insertion duct in the connection portion 22A and to reduce the concern of the interference between the movable component in the connection portion 22A and the voltage cable 32.

A fixed anode type in which the anode 52 is a fixed anode is used as the X-ray tube 36. The fixed anode type can be miniaturized because it does not have a rotating structure in a rotating anode type. In a case in which a plurality of X-ray tubes 36 are used, the overall size of the X-ray source 24 tends to be larger than that in a case in which one X-ray tube 36 is used. Therefore, in a case in which the size of the X-ray tube 36 is reduced, the size of the X-ray source 24 is also reduced, which is greatly advantageous. In addition, in a case in which the plurality of X-ray tubes 36 are arranged as in this example, as the diameter of the X-ray tube 36 becomes smaller, the arrangement interval of the X-ray tubes 36 can become shorter. Therefore, it is possible to further increase the density of the irradiation positions in the scanning angle KA.

Further, an X-ray tube 36 having a field-emission-type cathode 51 is used as the X-ray tube 36. The field-emission-type cathode 51 is a cold cathode type and generates a smaller amount of heat than a hot cathode type which heats a filament to emit thermal electrons. Therefore, since the number of members for heat countermeasures is reduced, it is easy to reduce the size of the X-ray tube 36. The advantages of reducing the size of the X-ray tube 36 are as described above.

In this example, the example in which tomosynthesis imaging is performed by the mammography apparatus 10 has been described. However, the mammography apparatus 10 can perform simple X-ray imaging in addition to the tomosynthesis imaging. The simple X-ray imaging means imaging which irradiates the breast BR with X-rays from the irradiation position where the irradiation angle SA of X-rays is approximately zero to obtain the projection image SP. The mammography apparatus 10 includes a plurality of X-ray tubes 36. In the mammography apparatus 10, for example, one X-ray tube 36 located at the center in the arrangement direction of the X-ray tubes 36, for example, one central X-ray tube 36(5) which is the fifth X-ray tube 36 from the end in the example illustrated in FIG. 6 is selected and the simple X-ray imaging is performed. In addition, instead of the simple X-ray imaging, an image combination process may be performed on the basis of a plurality of projection images SP acquired by the tomosynthesis imaging to generate a composite two-dimensional image equivalent to the image obtained by the simple X-ray imaging.

In this example, a plurality of X-ray tubes 36 are divided and accommodated in three units. However, the number of units 24A may be two or four or more. In addition, a plurality of X-ray tubes 36 may not be necessarily accommodated in each unit 24A and at least one X-ray tube 36 may be accommodated in each unit 24A. Of course, in a case in which a plurality of X-ray tubes 36 are accommodated in each unit, the number of housings 37, voltage connector cables 62, voltage connectors 64, signal connector cables 63, and signal connectors 65 is reduced. Therefore, this configuration contributes to reducing the size and cost of the X-ray source 24. In addition, different numbers of X-ray tubes 36 may be accommodated in each unit 24A. For example, five X-ray tubes 36 may be accommodated in one unit and six X-ray tubes 36 may be accommodated in another unit.

In the above-mentioned example, the X-ray source 24 includes nine X-ray tubes 36. However, the number of X-ray tubes 36 in the X-ray source 24 may be equal to or greater than two or equal to or less than eight or may be equal to or greater than ten.

For the irradiation order of the plurality of X-ray tubes 36, irradiation may sequentially be performed from the X-ray tube 36 disposed at one end in the arrangement direction. The irradiation order can be changed in various ways. For example, irradiation may be randomly performed such that the X-ray tube 36 disposed at the center emits radiation and then the X-ray tube 36 disposed at one end emits radiation.

In the mammography apparatus 10, the position and posture of the X-ray detector 26 are fixed during one tomosynthesis imaging operation.

In the above-mentioned example, a field-emission-type cold cathode is used as the cathode 51 of the X-ray tube 36. However, this type of X-ray tube 36 may not be used. For example, the X-ray tube 36 may be any type including a hot cathode in which a filament is heated to emit thermal electrons.

For example, the irradiation control of the X-ray tube including the hot cathode is performed as follows. First, a current flows to the filament to heat the filament. In this state, a high voltage is applied between the hot cathode and the anode. Then, thermal electrons are emitted from the hot cathode.

In the above-mentioned example, one voltage cable 32 is provided. However, a plurality of voltage cables 32 may be provided. In some cases, a plurality of voltage cables 32 are required according to, for example, the number of X-ray tubes 36. In this case, a distribution unit, such as the power distribution unit 61, is provided in the radiation source accommodation portion 25 to reduce the number of voltage cables 32 as compared to a case in which the distribution unit is not provided.

Modification Example 1 of Distribution Method

In the above-mentioned example, a method using the power distribution unit 61 has been described as the distribution method for distributing the voltage supplied through the voltage cable 32. However, as illustrated in FIG. 15, instead of using the power distribution unit 61, a daisy chain method may be used to distribute the voltage.

Figure 15:
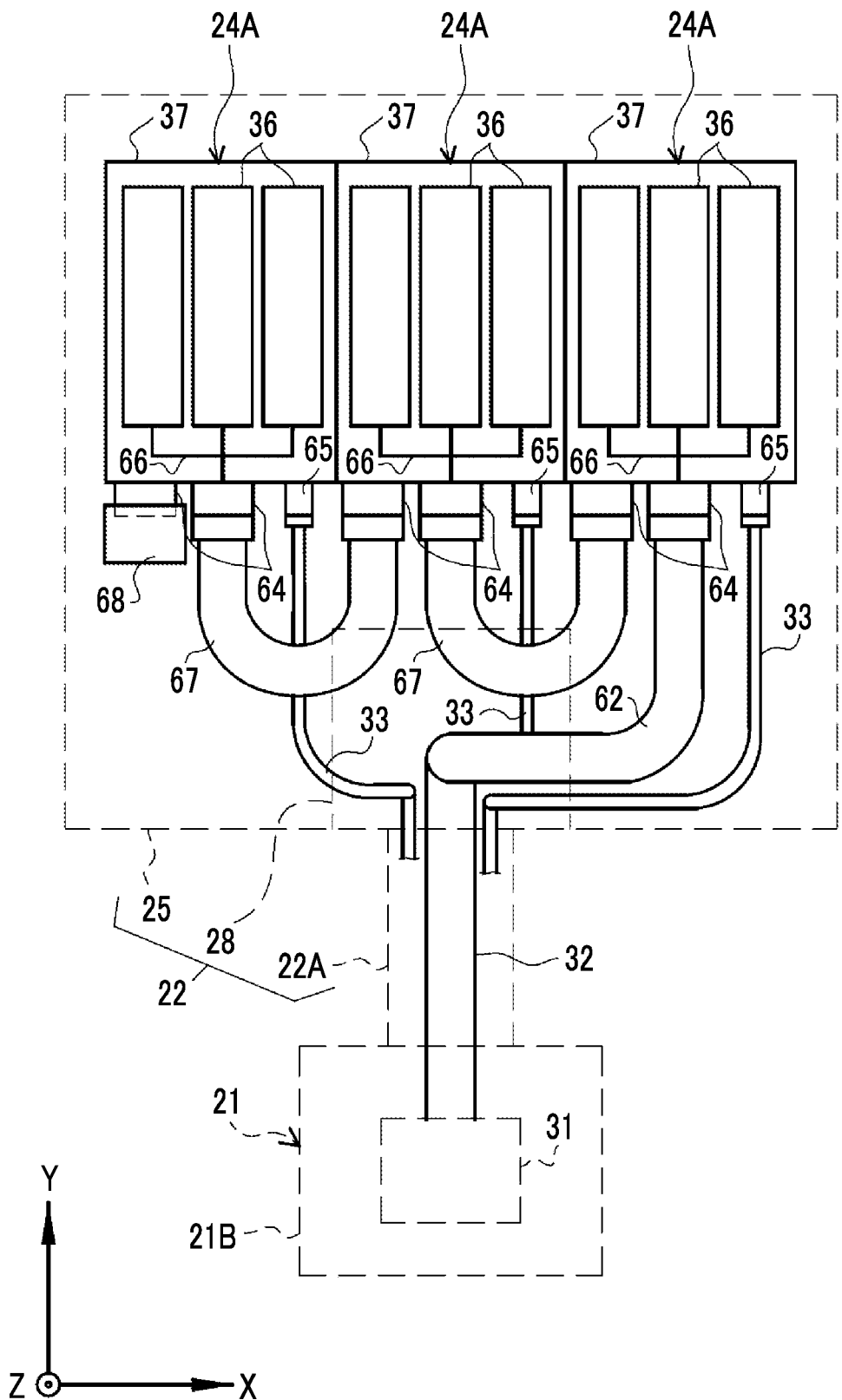
FIG. 15 is a diagram illustrating a distribution method using a daisy chain method.

In the example illustrated in FIG. 15, the power distribution unit 61 is not provided in the radiation source accommodation portion 25 unlike the example illustrated in FIG. 14. In addition, each unit 24A is provided with a plurality of voltage connectors 64 (two voltage connectors 64 in this example). The voltage cable 32 is connected to one of the plurality of units 24A. The voltage cable 32 is connected to one of the two voltage connectors 64 provided in the unit 24A. One end of a distribution cable 67 is connected to the other voltage connector 64. The other end of the distribution cable 67 is connected to one of two voltage connectors 64 of another unit 24A. The second and third units 24A are also connected by the daisy chain method. In this way, the voltage supplied from the voltage cable 32 is distributed to the plurality of units 24A. In a case in which the daisy chain method according to this example is used, the power distribution unit 61 is not required.

In this example, the first unit 24A connected to the voltage cable 32 corresponds to a first unit and the second and third units 24A correspond to a second unit. In the first unit, the voltage connector 64 connected to the distribution cable 67 corresponds to a distribution connector. In this example, the distribution unit that distributes the voltage from the first unit to another second unit using the daisy chain method includes the voltage connector 64 corresponding to the distribution connector and the distribution cable 67.

In FIG. 15, reference numeral 68 indicates a protective cap for closing and protecting one voltage connector 64 to which the distribution cable 67 is not connected in the third (right end) unit 24A.

In FIG. 15, the signal cable 33 is not distributed like the voltage cable 32 and three signal cables 33 are provided in correspondence with the three units 24A. The diameter of the signal cable 33 is less than the diameter of the voltage cable 32. Therefore, as in this example, the distribution unit for the voltage cable 32 may not be provided for the signal cable 33.

Modification Example 2 of Distribution Method

Figure 16:
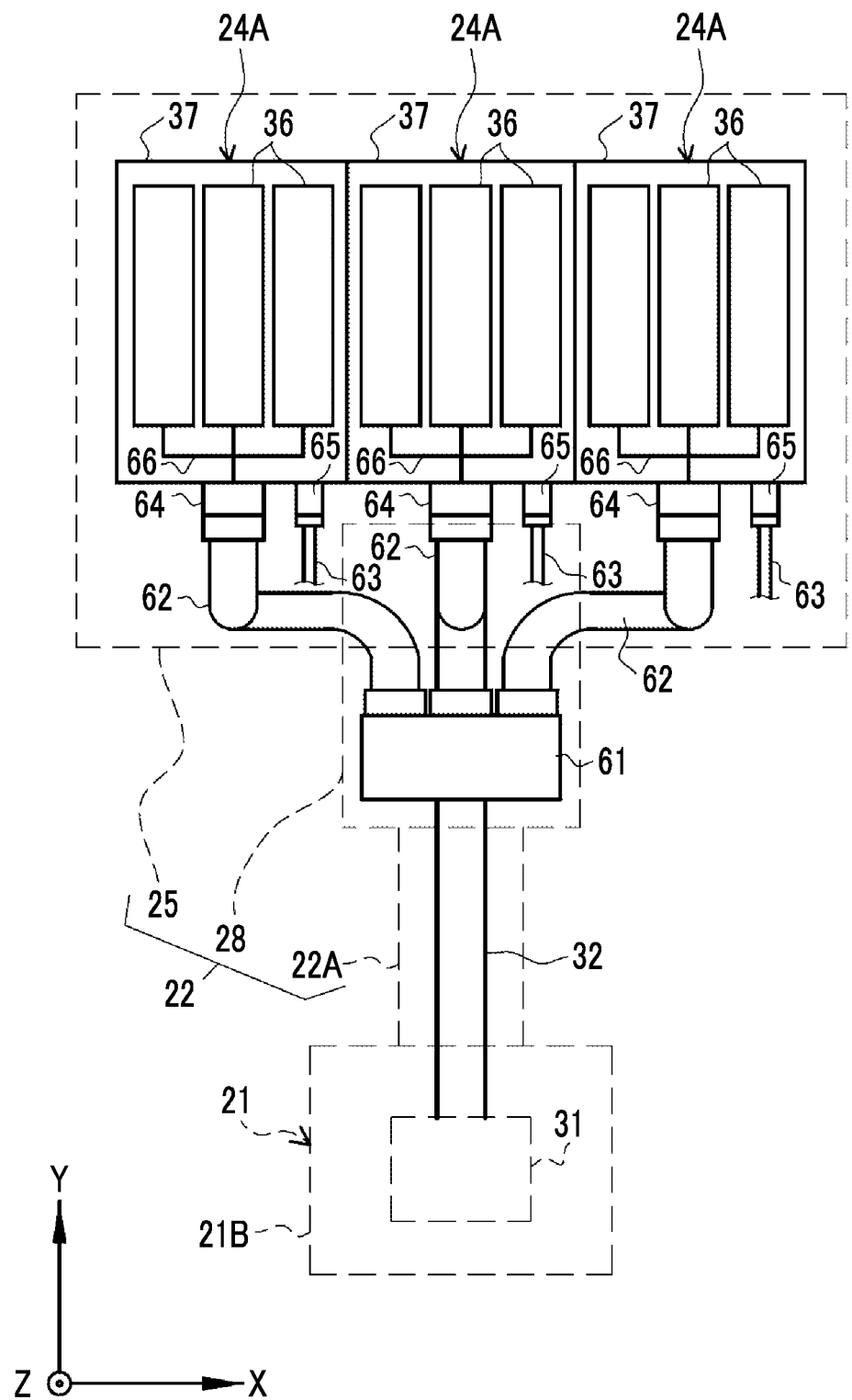
FIG. 16 is a diagram illustrating an example in which the power distribution unit is provided in an arm portion.

In an example illustrated in FIG. 16, the power distribution unit 61 is not provided in the radiation source accommodation portion 25, but is provided in the arm portion 28. As such, the power distribution unit 61 is not necessarily provided in the radiation source accommodation portion 25 and may be provided behind the connection portion 22A (close to the X-ray source 24) in the C-arm 22.

In FIG. 16, one end of each voltage connector cable 62 is connected to the power distribution unit 61 in the arm portion 28. Each voltage connector cable 62 extends into the radiation source accommodation portion 25 through the arm portion 28 and the other end of the voltage connector cable 62 is connected to the voltage connector 64 of each unit 24A. This holds for the signal connector cable 63.

Modification Example 3 of Distribution Method

Figure 17:
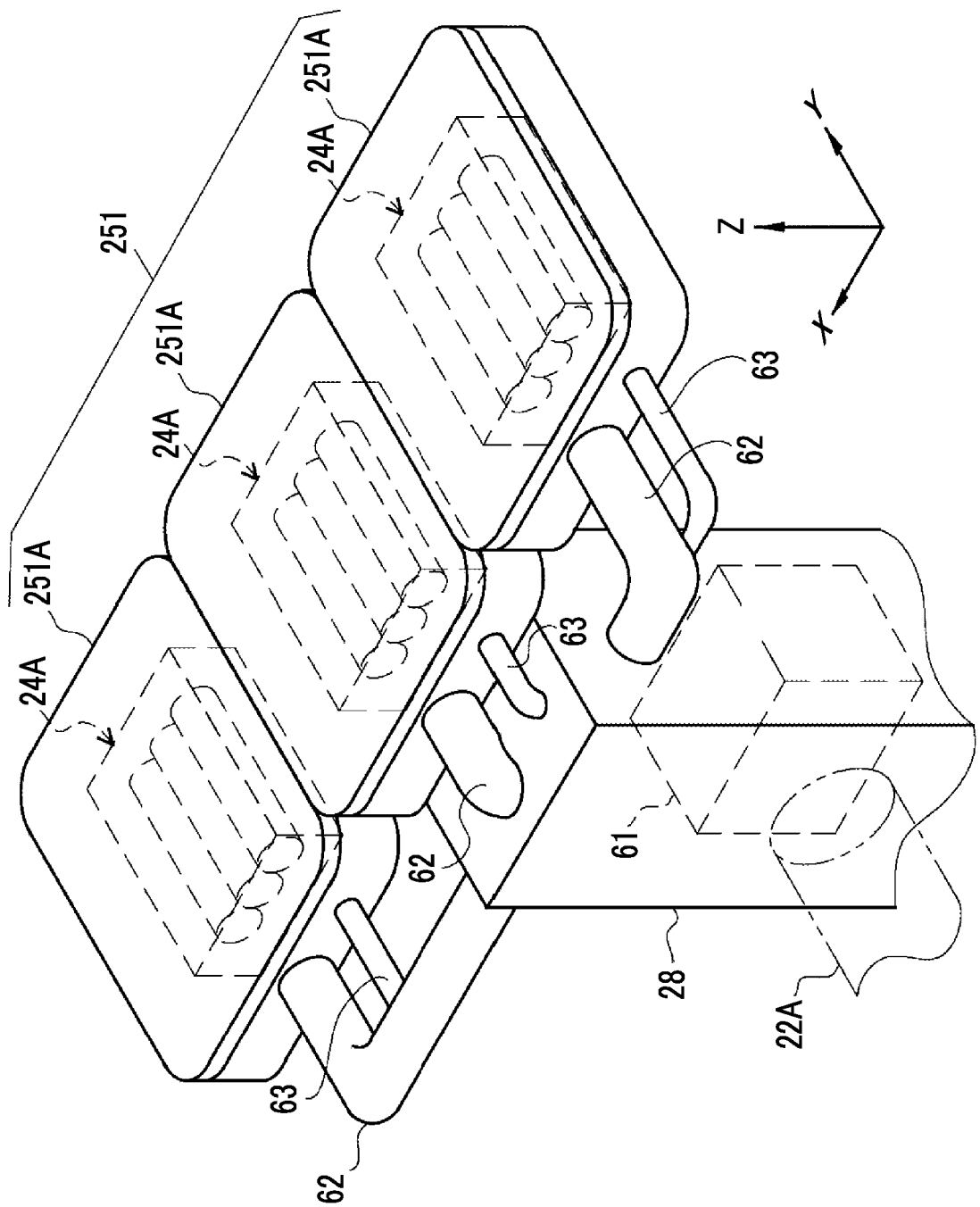
FIG. 17 is a diagram illustrating an example in which the radiation source accommodation portion is divided.

In an example illustrated in FIG. 17, a radiation source accommodation portion 251 includes a plurality of sub-radiation source accommodation portions 251A (three sub-radiation source accommodation portions 251A in this example). Each sub-radiation source accommodation portion 251A accommodates at least one of the units 24A. Among the three sub-radiation source accommodation portions 251A, for example, the sub-radiation source accommodation portion 251A disposed at the center is fixed to the arm portion 28 and the sub-radiation source accommodation portions 251A disposed on both sides are connected to the central sub-radiation source accommodation portion 25.

In FIG. 17, each sub-radiation source accommodation portion 251A accommodates one unit 24A. As such, in a case in which a plurality of sub-radiation source accommodation portions 251A are provided, for example, the power distribution unit 61 is provided in the arm portion 28 as in the example illustrated in FIG. 16. The voltage connector cable 62 extends from the power distribution unit 61 in the arm portion 28 to the outside of the arm portion 28 and then gets into each sub-radiation source accommodation portion 251A. As such, even in a case in which the radiation source accommodation portion 251 is divided into a plurality of sub-radiation source accommodation portions 251A, it is possible to use a distribution method using a distribution unit such as the power distribution unit 61.

Other Aspects of Radiography Apparatus

In the first embodiment, the mammography apparatus 10 has been described as an example of the radiography apparatus. In mammography, since the usability of tomosynthesis imaging is recognized, it is preferable to apply the radiography apparatus according to the present disclosure to the mammography apparatus 10. Of course, the radiography apparatus is not limited to the mammography apparatus 10 and may be applied to other imaging apparatuses.

Figure 18:
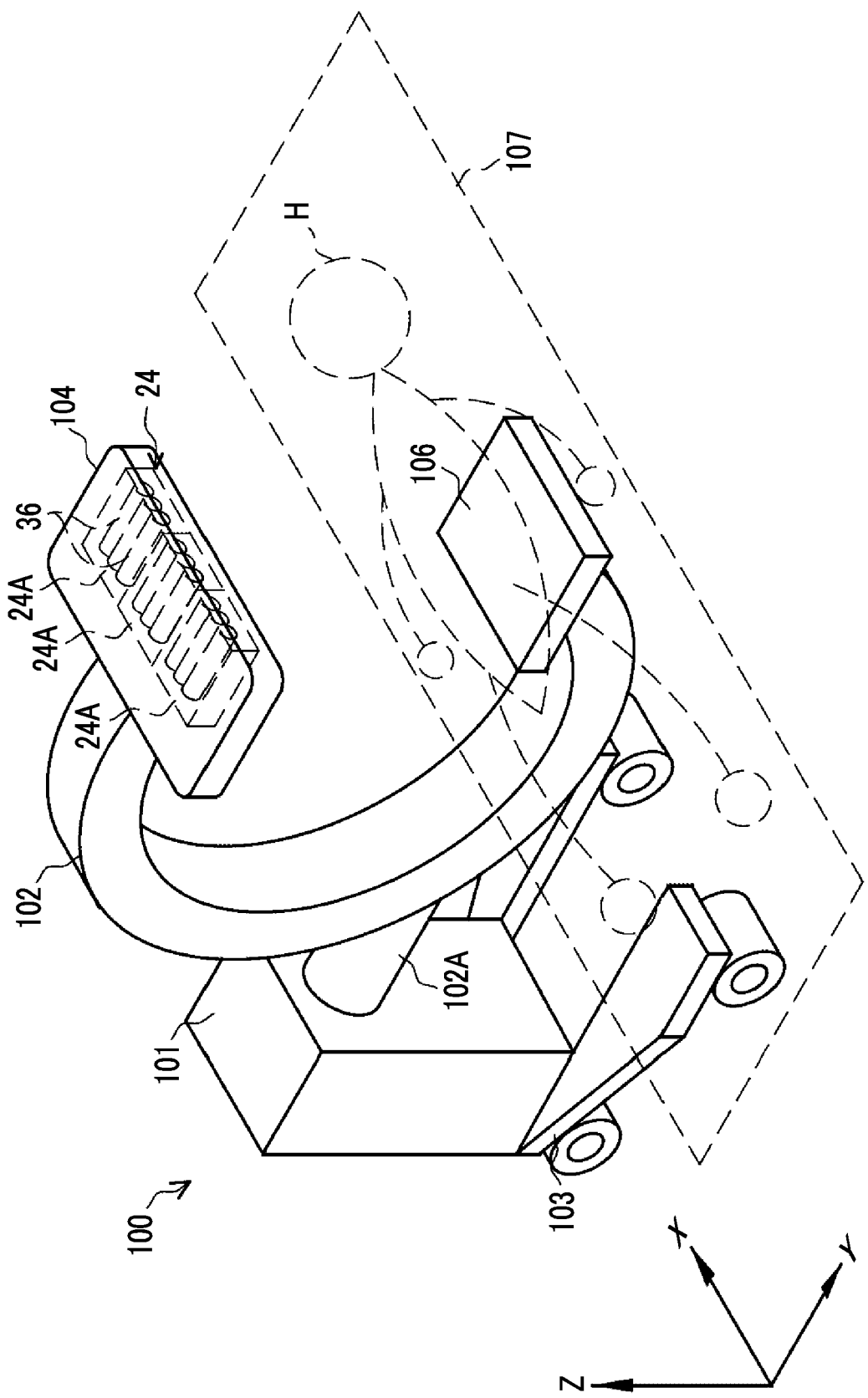
FIG. 18 is a diagram illustrating an X-ray imaging apparatus for surgery.

For example, as illustrated in FIG. 18, the radiography apparatus according to the present disclosure may be applied to an imaging apparatus 100 in addition to the mammography apparatus 10. The imaging apparatus 100 illustrated in FIG. 18 is an X-ray imaging apparatus that captures the image of a subject H during surgery.

The imaging apparatus 100 includes a main body 101 having a control device provided therein and a C-arm 102. The main body 101 is provided with a carriage 103. The C-arm 102 is provided with a radiation source accommodation portion 104 and a detector accommodation portion 106. The radiation source accommodation portion 104 and the detector accommodation portion 106 are held at the posture where they face each other as in the first embodiment.

The detector accommodation portion 106 is inserted below a bed 107 on which the subject H lies supine. The bed 107 is made of a material that transmits X-rays. The radiation source accommodation portion 104 is provided above the subject H at a position that faces the detector accommodation portion 106 with the subject H interposed therebetween.

An X-ray source 24 including a plurality of X-ray tubes 36 which is the same as the X-ray source 24 according to the first embodiment is provided in the radiation source accommodation portion 104. The X-ray source 24 includes a plurality of units 24A in which the plurality of X-ray tubes 36 are divided and accommodated. Therefore, similarly to the above-mentioned example, even in a case in which the plurality of X-ray tubes 36 are provided, the deterioration of maintenance is suppressed. Since the imaging range of the imaging apparatus 100 is wider than the range of the breast BR, the size of the X-ray tube 36 may be larger than the size of the X-ray tube 36 of the X-ray source 24 in the mammography apparatus 10 or the number of X-ray tubes 36 may be larger than that in the mammography apparatus 10.

The C-arm 102 includes a connection portion 102A that connects the C-arm 102 to the main body 101 so as to be displaceable with respect to the main body 101. Similarly to the C-arm 22 according to the first embodiment, the C-arm 102 is an example of the accommodation portion and the main body 101 is an example of the base. The high voltage generation device 31 is provided outside the C-arm 102. For example, the high voltage generation device 31 is provided in the main body 101. The voltage cable 32 is inserted into the connection portion 102A and extends into the C-arm 102. A distribution unit, such as the power distribution unit 61 illustrated in FIG. 14, is provided in the C-arm 102. Therefore, one voltage cable 32 inserted into the connection portion 102A is enough. As a result, similarly to the above-mentioned example, the effect of suppressing an increase in the diameter of a cable insertion duct of the connection portion 102A and suppressing the interference between the voltage cable 32 and a movable portion is obtained.

In the imaging apparatus 100, similarly to the mammography apparatus 10, it is possible to perform simple X-ray imaging in addition to tomosynthesis imaging. In addition, instead of performing the simple X-ray imaging, a composite two-dimensional image may be generated. Further, the imaging apparatus 100 may capture moving X-ray images in addition to still X-ray images.

The radiography apparatus according to the present disclosure may be applied to a general X-ray imaging apparatus configured by combining a ceiling-suspended X-ray source and an upright imaging table or a decubitus imaging table in addition to the configuration including the C-arm 102 such as the imaging apparatus 100. Further, the radiography apparatus may be applied to, for example, a cart-type mobile X-ray imaging apparatus which is moved to each hospital room and is used to capture the image of a patient.

In mammography apparatuses 10 according to the second and third embodiments illustrated in FIGS. 19 to 27, similarly to the first embodiment, an X-ray source including a plurality of X-ray tubes 36 includes a plurality of units in which the plurality of X-ray tubes 36 are divided and accommodated. In the following embodiments, the description of the same points as those in the first embodiment will not be repeated and the difference from the first embodiment will be mainly described.

Second Embodiment

Figure 19:
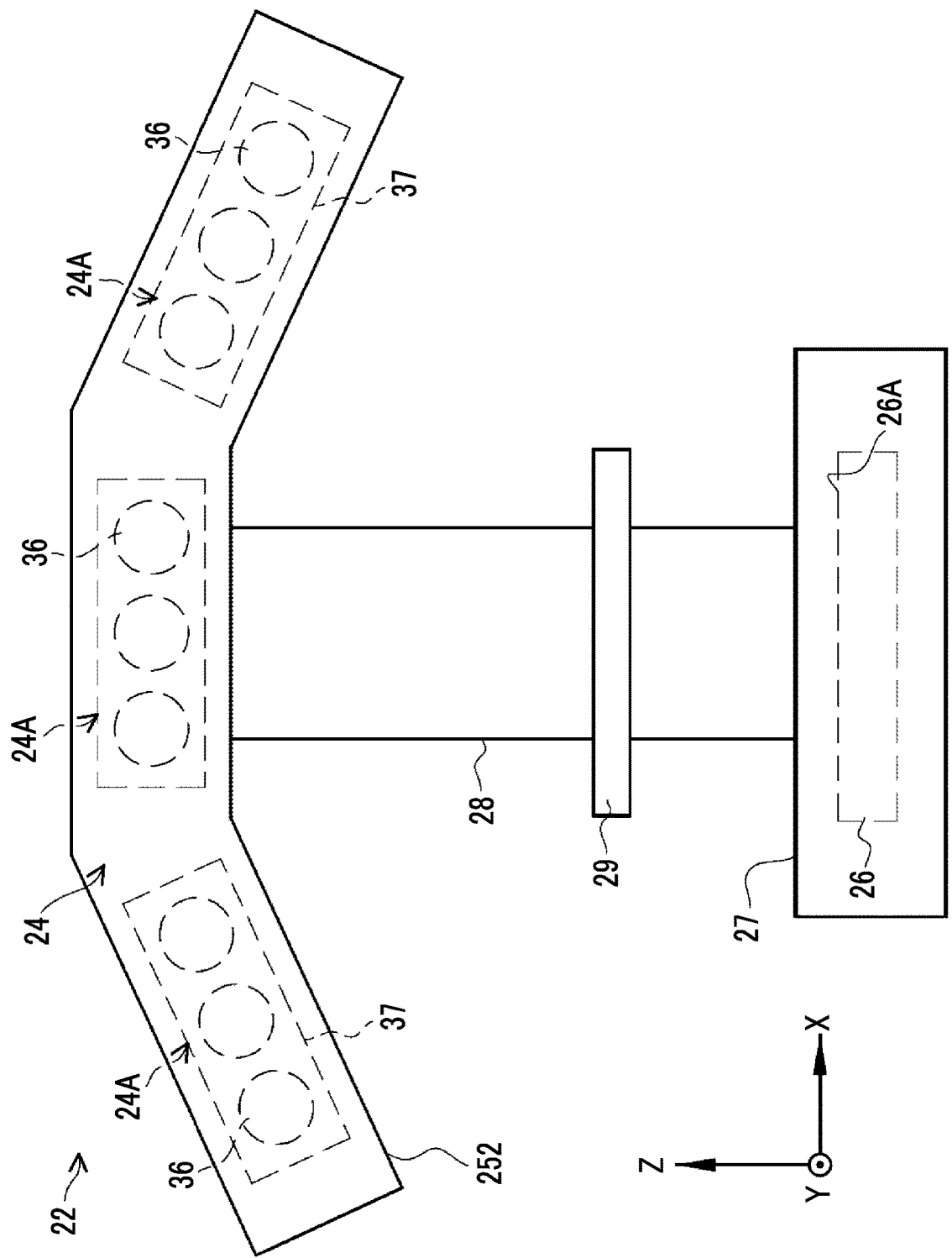
FIG. 19 is a diagram illustrating a second embodiment in which both ends of a radiation source accommodation portion are inclined.
Figure 20:
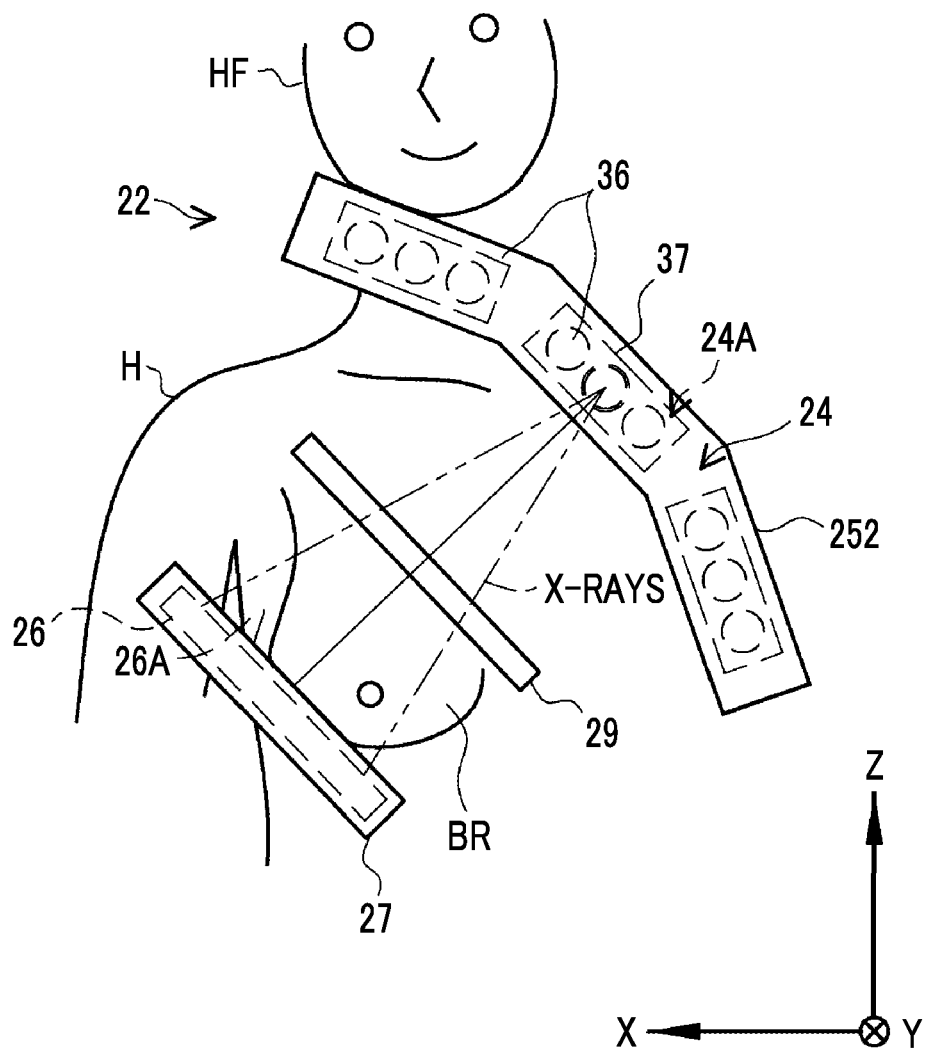
FIG. 20 is a diagram illustrating an aspect of MLO imaging using the radiation source accommodation portion illustrated in FIG. 19.
Figure 21:
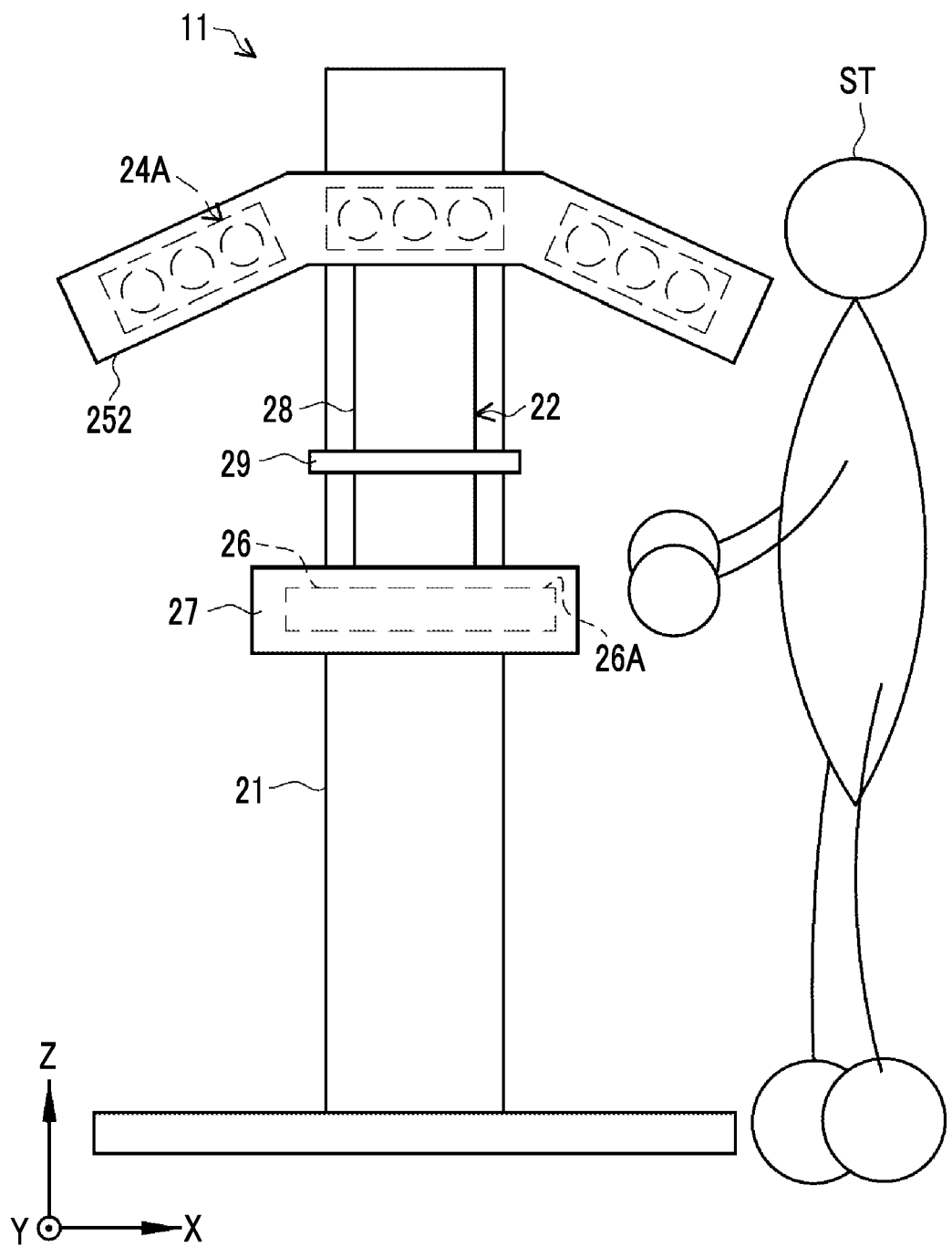
FIG. 21 is a diagram illustrating a direction in which a medical staff approaches.

An apparatus main body 11 of a mammography apparatus 10 according to the second embodiment illustrated in FIGS. 19 to 21 differs from the apparatus main body according to the first embodiment in the shape of a radiation source accommodation portion 252 of a C-arm 22. Both ends of the radiation source accommodation portion 252 in the arrangement direction (X direction) of a plurality of X-ray tubes 36 are inclined toward the X-ray detector 26. In a case in which the X-ray source 24 has a shape in which a plurality of X-ray tubes 36 are arranged, the radiation source accommodation portion 252 has a large width in the arrangement direction. In a case in which both ends of the radiation source accommodation portion 252 are inclined, the following effects are obtained.

First, in a case in which MLO imaging is performed as illustrated in FIG. 20, since the C-arm 22 is rotated on the Y-axis, the radiation source accommodation portion 252 is also rotated. Then, one end of the radiation source accommodation portion 252 is located in the vicinity of a face HF of the subject H. In a case in which both ends of the radiation source accommodation portion 252 are inclined, it is easy to retract the face HF so as not to face the radiation source accommodation portion 252, for example, such that the jaw is placed on the upper surface of the radiation source accommodation portion 252. Therefore, according to this example, the posture of the subject H can be eased during tomosynthesis imaging.

As illustrated in FIG. 21, in a case in which the medical staff ST, such as a doctor or a radiology technician, positions the subject H with respect to the apparatus main body 11 of the mammography apparatus 10, the medical staff ST approaches a detector accommodation portion 27 which functions as an imaging table, a compression plate 29, and the subject H from the end side of the radiation source accommodation portion 252. Therefore, in a case in which both ends of the radiation source accommodation portion 252 are inclined, the protrusion of the radiation source accommodation portion 252 toward both ends is suppressed, as compared to a case in which both ends of the radiation source accommodation portion 252 are not inclined. As a result, it is easy for the medical staff ST to approach, for example, the subject H and to perform positioning.

Further, the radiation source accommodation portion 252 according to this example may be divided into a plurality of sub-radiation source accommodation portions like the radiation source accommodation portion 251 illustrated in FIG. 17.

Figure 22:
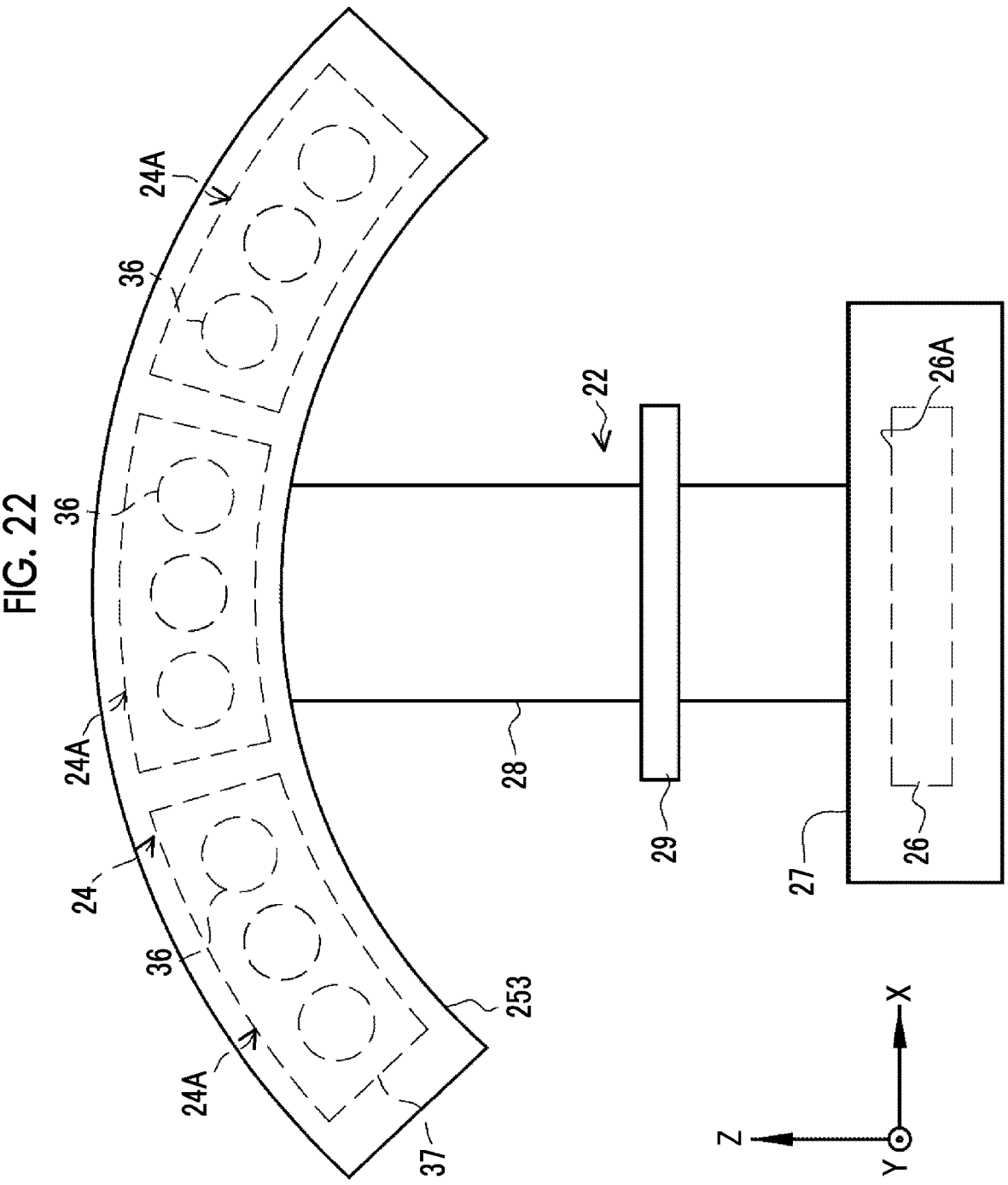
FIG. 22 is a diagram illustrating an arc-shaped radiation source accommodation portion.

The aspect in which both ends of the radiation source accommodation portion are inclined includes an aspect in which the entire radiation source accommodation portion 253 is formed in an arc shape such that both ends are curved as illustrated in FIG. 22 in addition to the aspect in which both ends of the radiation source accommodation portion 252 are linearly inclined as illustrated in FIGS. 19 to 21. In the aspect in which both ends are curved, the same effect as that in the radiation source accommodation portion 252 is obtained.

Third Embodiment

In the third embodiment illustrated in FIGS. 23 to 27, at least one of radiation source accommodation portions can be displaced with respect to an arm portion 28 corresponding to a support portion and a detector accommodation portion 27.

Figure 23:
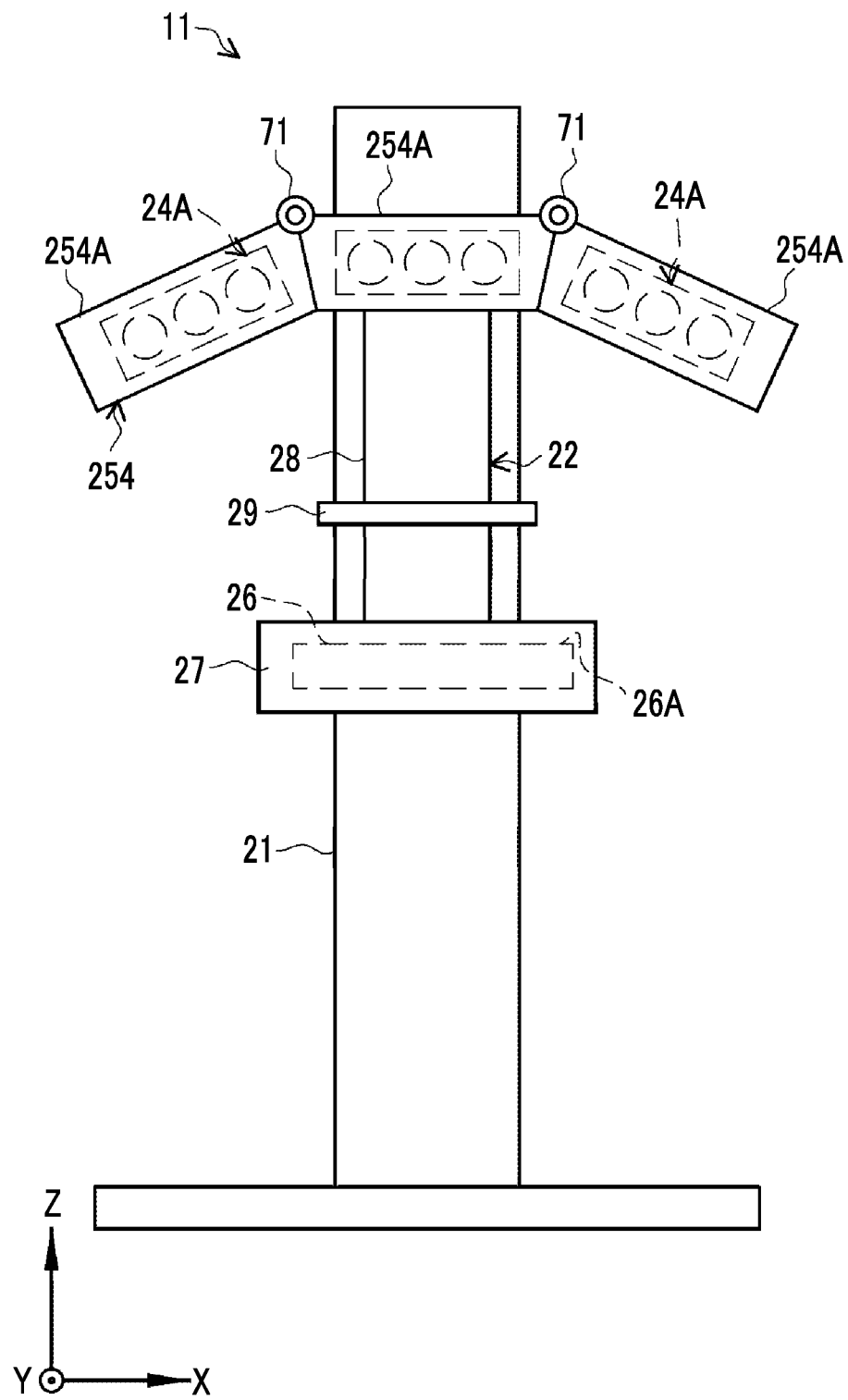
FIG. 23 is a diagram illustrating a third embodiment in which both ends of a radiation source accommodation portion are displaced.

A radiation source accommodation portion 254 illustrated in FIG. 23 is divided into three sub-radiation source accommodation portions 254A like the radiation source accommodation portion 251 illustrated in FIG. 17. Each sub-radiation source accommodation portion 254A accommodates one unit 24A forming the X-ray source 24. The three sub-radiation source accommodation portions 254A are arranged in the arrangement direction (X direction) of the X-ray tubes 36.

In an initial state illustrated in FIG. 23, both ends of the radiation source accommodation portion 254 in the arrangement direction (X direction) are inclined toward the X-ray detector 26 like the radiation source accommodation portion 252 illustrated in FIG. 19. Specifically, two sub-radiation source accommodation portions 254A disposed on both sides of the sub-radiation source accommodation portion 254A disposed at the center are disposed at the posture where the free ends thereof are inclined toward the X-ray detector 26.

The central sub-radiation source accommodation portion 254A is fixed to the arm portion 28 of the C-arm 22. The sub-radiation source accommodation portions 254A disposed on both sides are attached to the central sub-radiation source accommodation portion 254A through hinges 71 so as to be rotatable on the Y-axis.

Figure 24:
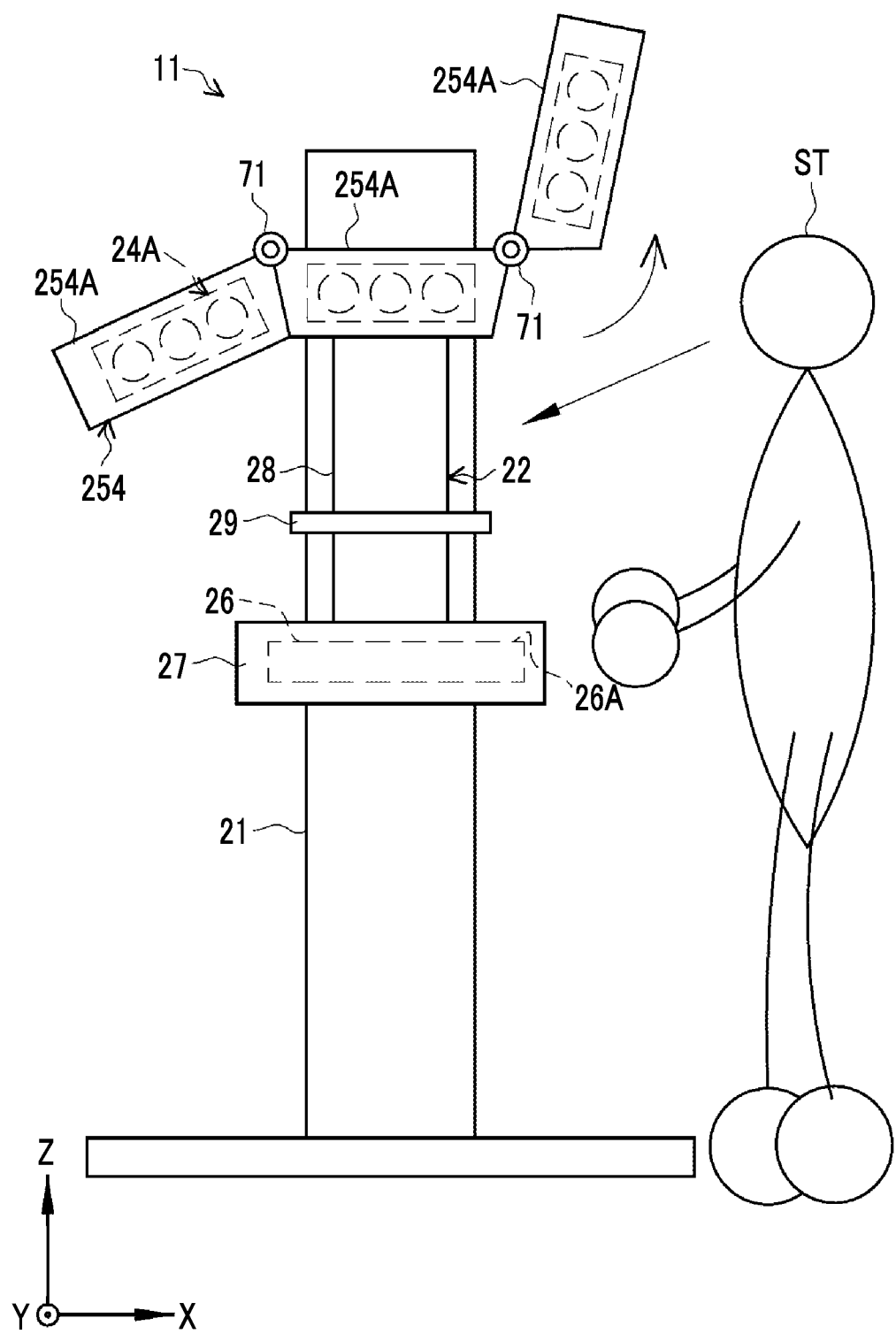
FIG. 24 is a diagram illustrating a state in which the end of the radiation source accommodation portion illustrated in FIG. 23 is retracted.

As illustrated in FIG. 24, the sub-radiation source accommodation portions 254A disposed on both sides are rotated around the hinges 71 as the rotation centers in a direction away from the X-ray detector 26. In the example illustrated in FIG. 24, the right sub-radiation source accommodation portion 254A is rotated around the hinge 71 in the counterclockwise direction so as to be flipped up. In a case in which the X-ray source 24 in which a plurality of X-ray tubes 36 are arranged is used, the width of the radiation source accommodation portion 254 in the arrangement direction (X direction) of the X-ray tubes 36 is large and both ends of the radiation source accommodation portion 254 protrude to the side of the apparatus main body 11 of the mammography apparatus 10. In this example, the sub-radiation source accommodation portions 254A on both sides in the arrangement direction (X direction) are rotated to retract the ends of the radiation source accommodation portion 254 which protrude to the side to the upper side of the apparatus main body 11. This configuration makes it easy for the medical staff ST to approach the detector accommodation portion 27, the compression plate 29, and the subject H from the side of the apparatus main body 11 during positioning.

In this example, the sub-radiation source accommodation portions 254A disposed on both sides can be rotated around the hinges 71. However, not the sub-radiation source accommodation portions 254A disposed on both sides but only the sub-radiation source accommodation portion 254A disposed on only one side may be rotated. Of course, it is preferable to rotate the sub-radiation source accommodation portions 254A disposed on both sides since the left and right breasts BR are present.

Modification Example 1 of Third Embodiment

Figure 25:
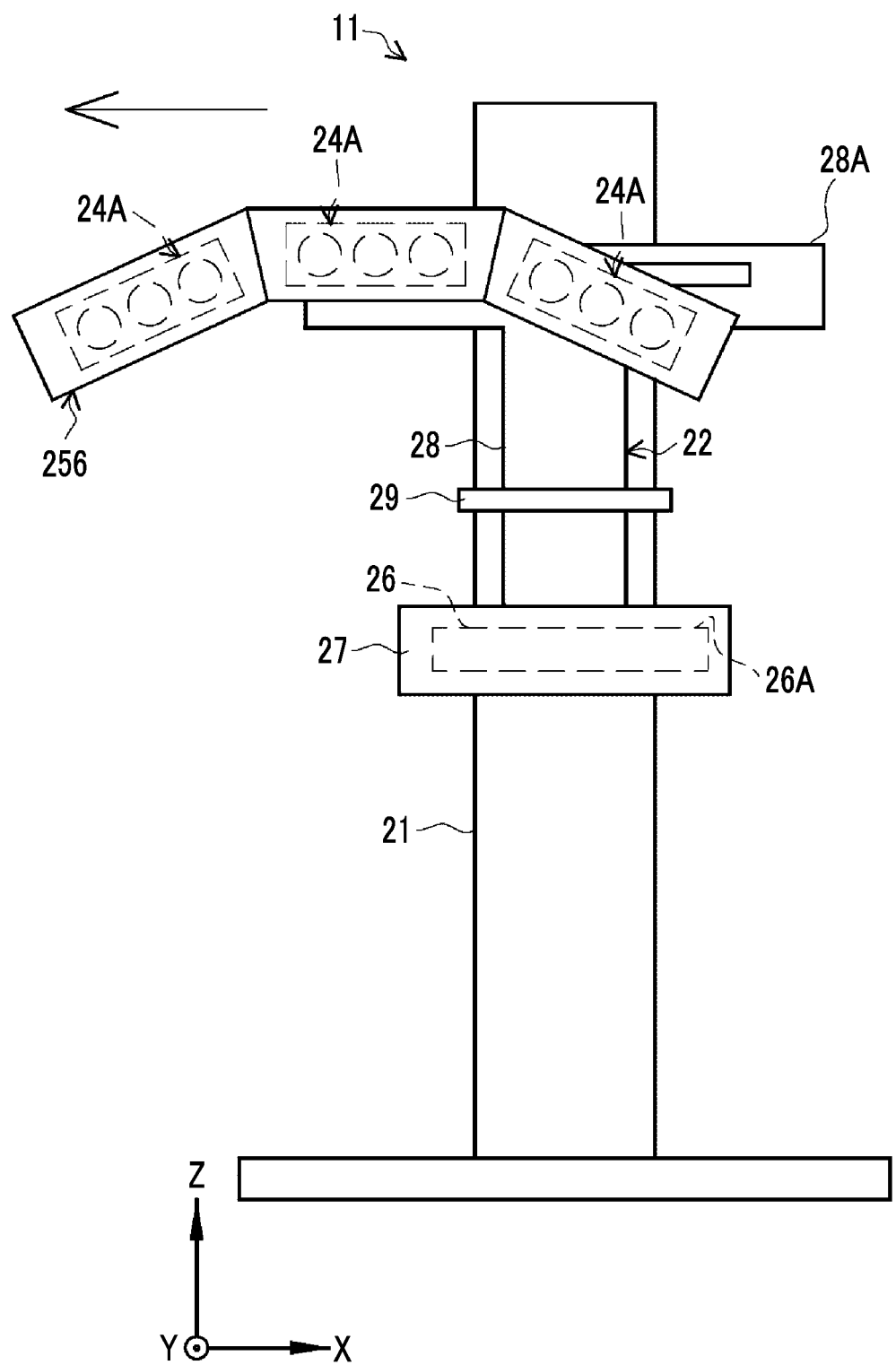
FIG. 25 is a diagram illustrating an aspect in which the radiation source accommodation portion is slid in a lateral direction.

The radiation source accommodation portion may be configured so as to be slidable in a plane parallel to the imaging surface 26A along the arrangement direction (X direction) of the X-ray tubes 36 like a radiation source accommodation portion 256 illustrated in FIG. 25. That is, in the example illustrated in FIG. 25, the radiation source accommodation portion 256 is slid in the lateral direction of the apparatus main body 11. In this example, the arm portion 28 of the C-arm 22 is provided with a rail member 28A that extends in the X direction. The radiation source accommodation portion 256 is attached to the rail member 28A so as to be slidable. Therefore, during positioning, it is possible to retract the radiation source accommodation portion 256 in a direction opposite to the direction in which the medical staff ST approaches the apparatus main body 11. As a result, it is easy for the medical staff ST to approach, for example, the subject H and the same effects as those in the radiation source accommodation portion 254 illustrated in FIGS. 23 and 24 are obtained.

Modification Example 2 of Third Embodiment

Figure 26:
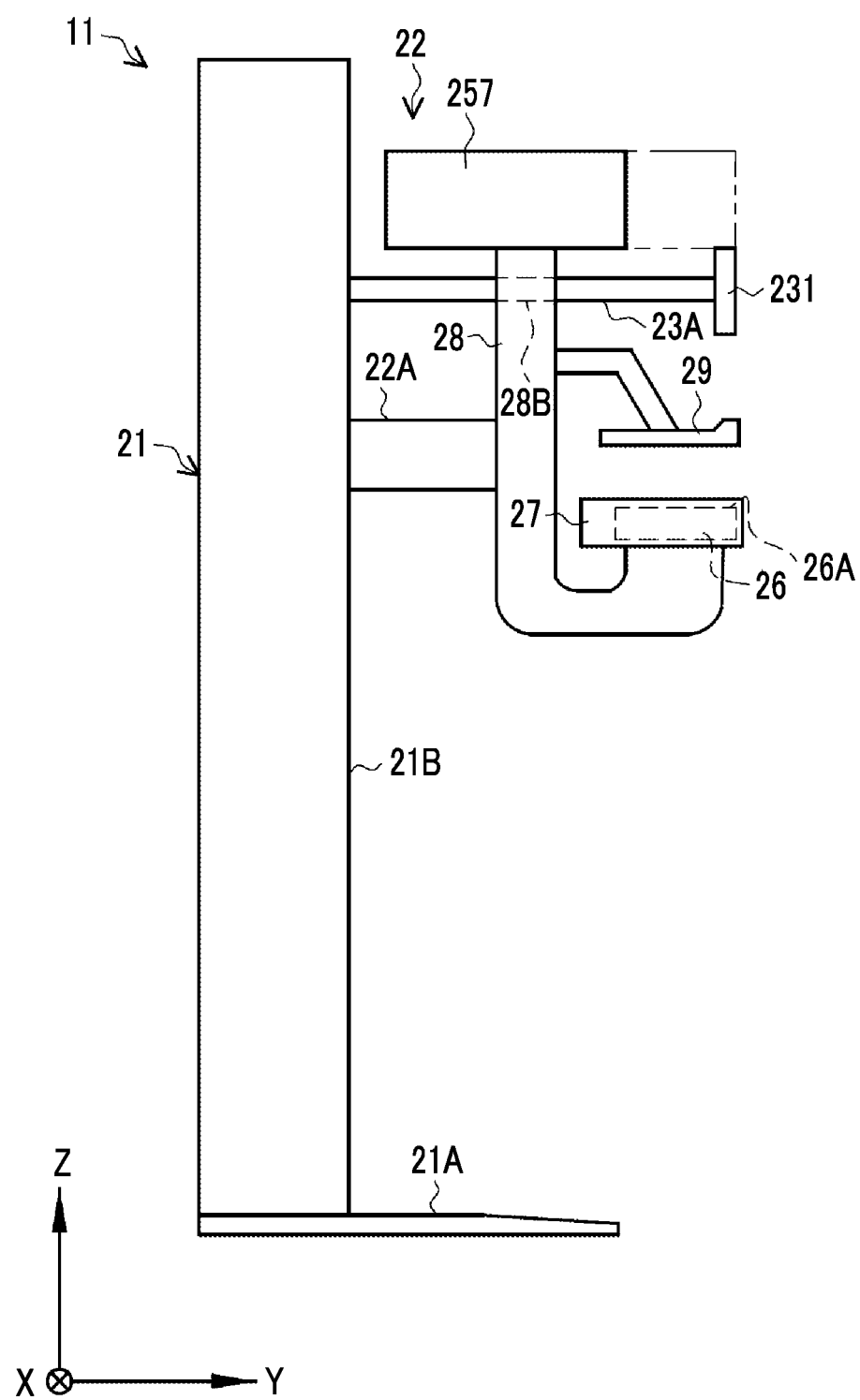
FIG. 26 is a diagram illustrating an aspect in which the radiation source accommodation portion is slid backward.

The radiation source accommodation portion may be configured so as to be slidable in a plane parallel to the imaging surface 26A along a direction (Y direction) perpendicular to the arrangement direction (X direction) of a plurality of X-ray tubes 36 like a radiation source accommodation portion 257 illustrated in FIG. 26. That is, in a case in which the side of the support 21B is the rear side and the side of the radiation source accommodation portion 257 is the front side in the apparatus main body 11, in the example illustrated in FIG. 26, the radiation source accommodation portion 257 is slid in the front-rear direction of the apparatus main body 11. With this configuration, as illustrated in FIG. 26, the radiation source accommodation portion 257 can be retracted from an initial position represented by a two-dot chain line to a retracted position which is represented by a solid line and is close to the support 21B behind the radiation source accommodation portion 257. Therefore, since the space above the detector accommodation portion 27 and the compression plate 29 is open, the medical staff ST can easily approach, for example, the subject H during positioning.

In the example illustrated in FIG. 26, a face guard 231 is not fixed to the C-arm 22, but is fixed to the support 21B. The face guard 231 is provided with an attachment shaft 23A that extends backward to the support 21B. The attachment shaft 23A extends to the support 21B through a through hole 28B that is formed in the arm portion 28 of the C-arm 22. The through hole 28B is formed in an arc shape so as to avoid interference with the attachment shaft 23A in a case in which the C-arm 22 is rotated on the Y-axis. Therefore, even in a case in which the C-arm 22 is rotated on the Y-axis, the face guard 231 is not rotated in operative association with the rotation of the C-arm 22 and can be fixed. Since the face guard 231 protects the face of the positioned subject H from X-rays, it is preferable that the face guard 231 is fixed in front of the face of the subject H even in a case in which the C-arm 22 is rotated.

It is considered that it is easy to simplify the structure of the configuration which is slid to the support 21B to be retracted, such as the radiation source accommodation portion 257 according to this example, as a configuration for retracting the radiation source accommodation portion in consideration of a combination with the fixed face guard 231, which is preferable.

Modification Example 3 of Third Embodiment

Figure 27:
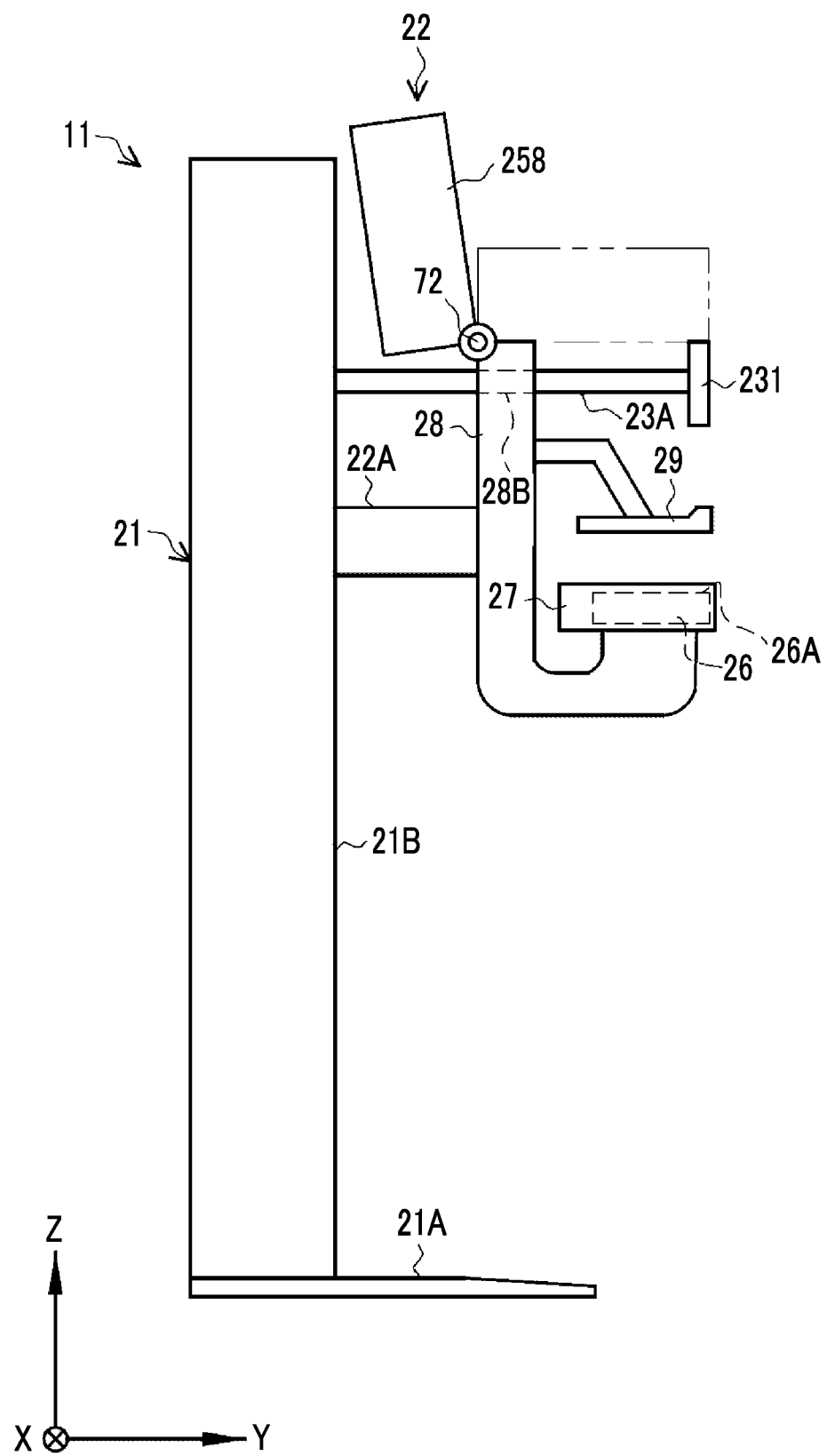
FIG. 27 is a diagram illustrating an aspect in which the radiation source accommodation portion is flipped up backward.

A radiation source accommodation portion 258 illustrated in FIG. 27 is attached to the arm portion 28 corresponding to a support portion through a hinge 72 so as to be rotatable on the X-axis. In a case in which an end of the radiation source accommodation portion 258 which is close to the arm portion 28 is referred to as the rear end, a leading end which is a free end opposite to the rear end is rotatable around the hinge 72 in the direction away from the X-ray detector 28. That is, the radiation source accommodation portion 258 is rotated so as to be flipped up to the rear side of the apparatus main body 11. As such, in a case in which the radiation source accommodation portion 258 is retracted from an initial position represented by a two-dot chain line to a retracted position represented by a solid line, a space above the detector accommodation portion 27, the compression plate 29, and the subject H is open. Therefore, similarly to the example illustrated in FIG. 26, it is easy for the medical staff ST to approach, for example, the subject H during positioning.

In the technology according to the present disclosure, the above-mentioned various embodiments or various modification examples may be appropriately combined with each other. For example, in the third embodiment illustrated in FIGS. 23 to 25, instead of the radiation source accommodation portions 254 and 256 in which both ends are inclined, a radiation source accommodation portion in which both ends are not inclined, such as the radiation source accommodation portion 25 illustrated in FIG. 11 or the radiation source accommodation portion 251 illustrated in FIG. 17, may be used. In addition, the voltage distribution unit described in the first embodiment may be combined with the second embodiment and the third embodiment. Further, the face guard 231 illustrated in FIG. 23 may be applied to the first embodiment and the second embodiment.

In each of the above-described embodiments, the example in which tomosynthesis imaging is performed with the plurality of X-ray tubes 36 completed fixed has been described. However, for example, tomosynthesis imaging may be performed while the plurality of X-ray tubes 36 are being moved in the arrangement direction (X direction) of the X-ray tubes 36 in the range of the arrangement interval of the X-ray tubes 36. In this case, the density of the X-ray irradiation positions in the scanning angle KA is high, and the number of artifacts in the tomographic image can be reduced as the number of projection images SP increases. The arrangement interval of the plurality of X-ray tubes 36 may be reduced in order to increase the density of the irradiation positions. However, the reduction in the arrangement interval of the X-ray tubes 36 is limited by, for example, the diameter of the X-ray tube 36. Therefore, the plurality of X-ray tubes 36 are moved in the range of the arrangement interval to increase the density of the irradiation positions in the scanning angle KA.

In this case, it is possible to reduce the imaging time since the movement range of the X-ray tube 36 is narrower than that in a case in which one X-ray tube 36 is moved in the entire range of the scanning angle KA. In addition, in a case in which the plurality of X-ray tubes 36 are moved, all of the units 24A may be collectively moved or the units 24A may be individually moved.

In each of the above-described embodiments, the X-ray tube 36 with one focus F has been described as an example of the X-ray tube. However, as illustrated in FIG. 28, an X-ray tube 361 with a plurality of focuses F1 and F2 may be used as the X-ray tube. In a case in which the X-ray tube 361 illustrated in FIG. 28 is used, the density of the irradiation positions can be higher than that in a case in which the X-ray tube with one focus F is used. As illustrated in FIG. 28, a plurality of X-ray tubes 361 are divided and accommodated in a plurality of units 24A.

For example, the X-ray tube 36 in which the field-emission-type cathode 51 illustrated in FIG. 10 has a plurality of electron emission areas (emitter electrodes 51A) can be used as the X-ray tube 361. The electron emission area is controlled by selecting the gate electrode 51B applying the gate voltage. The electron emission areas are switched to switch between the positions where electrons collide in the anode 52, that is, between the focuses F1 and F2.

In addition, an X-ray tube which includes a plurality of cathodes 51 and in which the cathodes 51 are switched to switch between the focuses F1 and F2 may be used as the X-ray tube 361. Further, an X-ray tube in which the trajectory of electrons emitted by one cathode 51 is changed by a deflector to switch between the focuses F1 and F2 may be used as the X-ray tube 361. The deflector changes the trajectory of electrons using the action of the electric field or the magnetic field. In the case of the X-ray tube 361, not only the cold cathode type but also a hot cathode type having a filament may be used.

Here, the X-ray tube 361 having two focuses, that is, the focuses F1 and F2 has been described as an example. However, the number of focuses may be two or more.

Further, all of the plurality of X-ray tubes in the X-ray source 24 may not have a plurality of focuses or at least one of the plurality of x-ray tubes may have a plurality of focuses.

In each of the above-described embodiments, the mammography apparatus 10 and the imaging apparatus 100 (see FIG. 18) having a tomosynthesis imaging function have been described as an example of the radiography apparatus according to the present disclosure. However, the radiography apparatus according to the present disclosure can be applied to radiography apparatuses without a tomosynthesis imaging function as long as the radiography apparatuses have a plurality of X-ray tubes.

In each of the above-described embodiments, the imaging apparatus using X-rays as radiation have been described as an example. However, an imaging apparatus using γ-rays may be described as an example. In addition, the present disclosure is not limited to the above-described embodiments and various configurations can be used without departing from the scope and spirit of the present disclosure.

What is claimed is:

1. A radiography apparatus comprising:
a radiation detector having an imaging surface that detects radiation transmitted through an object and captures a projection image of the object; and
a radiation source that has a plurality of radiation tubes which emit the radiation to the imaging surface at different irradiation angles, selectively irradiates the object with the radiation from the plurality of radiation tubes, and includes a plurality of units in which the plurality of radiation tubes are divided and accommodated,
wherein each of the plurality of units comprises a housing and is individually replaceable.

2. The radiography apparatus according to claim 1,
wherein the plurality of radiation tubes are arranged in a row in the radiation source.

3. The radiography apparatus according to claim 1, further comprising:
an accommodation portion that accommodates the radiation source and the radiation detector at a posture where the radiation source and the radiation detector face each other; and
a connection portion that connects the accommodation portion to a base such that the accommodation portion is displaceable with respect to the base.

4. The radiography apparatus according to claim 3, further comprising:
a voltage generation device that is provided outside the accommodation portion;
at least one voltage cable that supplies a voltage generated by the voltage generation device to the radiation source and extends from the voltage generation device into the accommodation portion through the connection portion; and
a distribution unit that is provided in the accommodation portion and distributes the voltage supplied through the voltage cable to each of the plurality of units of the radiation source.

5. The radiography apparatus according to claim 4,
wherein the distribution unit is a power distribution unit that includes a plurality of connectors for connection to each of the plurality of units and distributes the voltage supplied through the voltage cable to the plurality of units.

6. The radiography apparatus according to claim 4,
wherein the voltage cable is connected to one first unit among the plurality of units, and
the distribution unit distributes the voltage from the first unit connected to the voltage cable to other second units using a daisy chain method and includes a distribution connector provided in the first unit and a distribution cable connected to the distribution connector.

7. The radiography apparatus according to claim 3,
wherein the accommodation portion includes a radiation source accommodation portion accommodating the radiation source and including a plurality of sub-radiation source accommodation portions each of which accommodates at least one of the units.

8. The radiography apparatus according to claim 3,
wherein the object is a breast.

9. The radiography apparatus according to claim 8,
wherein the accommodation portion includes a radiation source accommodation portion that accommodates the radiation source, and
both ends of the radiation source accommodation portion in an arrangement direction of the plurality of radiation tubes are inclined toward the radiation detector.

10. The radiography apparatus according to claim 8,
wherein the accommodation portion includes a radiation source accommodation portion that accommodates the radiation source, a detector accommodation portion that accommodates the radiation detector, and a support portion that integrally supports the radiation source accommodation portion and the detector accommodation portion, and
at least a part of the radiation source accommodation portion is displaceable with respect to the support portion and the detector accommodation portion.

11. The radiography apparatus according to claim 10,
wherein at least one of both ends of the radiation source accommodation portion in an arrangement direction of the plurality of radiation tubes is displaceable in a direction away from the radiation detector.

12. The radiography apparatus according to claim 10,
wherein the radiation source accommodation portion is slidable along the arrangement direction of the plurality of radiation tubes in a plane parallel to the imaging surface.

13. The radiography apparatus according to claim 10,
wherein the radiation source accommodation portion is slidable along a direction perpendicular to the arrangement direction of the plurality of radiation tubes in a plane parallel to the imaging surface.

14. The radiography apparatus according to claim 10,
wherein, in a case in which an end of the radiation source accommodation portion which is close to the support portion is a rear end, a leading end of the radiation source accommodation portion which is a free end opposite to the rear end is rotatable around the rear end in a direction away from the radiation detector.

15. The radiography apparatus according to claim 1,
wherein the radiation tube includes a cathode that emits electrons and an anode that emits radiation from a focus where the electrons emitted from the cathode collide.

16. The radiography apparatus according to claim 15,
wherein the anode is a fixed anode.

17. The radiography apparatus according to claim 15,
wherein the cathode is a field emission type that emits an electron beam using a field emission phenomenon which occurs in a case in which an electric field is applied to a surface of a conductor.

18. The radiography apparatus according to claim 15,
wherein at least one of the plurality of radiation tubes has a plurality of the focuses.

19. The radiography apparatus according to claim 1,
wherein the radiography apparatus has a tomosynthesis imaging function which selectively performs the emission of the radiation from the plurality of radiation tubes to acquire a plurality of the projection images based on the emission of the radiation in order to obtain a tomographic image of the object on the basis of the plurality of projection images.

20. The radiography apparatus according to claim 19,
wherein, during one tomosynthesis imaging operation, a position and posture of the radiation detector are fixed.

21. The radiography apparatus according to claim 4,
wherein the plurality of units are connected to the distribution unit via connectors, with one of the connectors being provided for each of the plurality of units.

* * * * *